United States Patent
Nakayama et al.

(10) Patent No.: US 8,838,207 B2
(45) Date of Patent: Sep. 16, 2014

(54) RADIOGRAPHIC IMAGE CAPTURING APPARATUS

(75) Inventors: Hiroki Nakayama, Ashigarakami-gun (JP); Hajime Nakata, Ashigarakami-gun (JP); Naoyuki Okada, Ashigarakami-gun (JP); Takao Yoshida, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 299 days.

(21) Appl. No.: 12/840,810

(22) Filed: Jul. 21, 2010

(65) Prior Publication Data
US 2011/0021947 A1 Jan. 27, 2011

(30) Foreign Application Priority Data

Jul. 24, 2009 (JP) .................................. 2009-172740

(51) Int. Cl.
*A61B 6/04* (2006.01)
*A61B 6/00* (2006.01)

(52) U.S. Cl.
CPC ............... *A61B 6/0414* (2013.01); *A61B 6/469* (2013.01); *A61B 6/502* (2013.01)
USPC ........... 600/425; 600/427; 600/562; 600/567; 600/568; 378/37; 378/147

(58) Field of Classification Search
USPC ................. 600/407, 425, 427, 562, 567, 568; 378/37, 147
See application file for complete search history.

(56) References Cited

U.S. PATENT DOCUMENTS

| 7,443,949 B2 | 10/2008 | Defreitas et al. |
| 7,443,950 B2 | 10/2008 | Sendai |
| 7,613,276 B2 | 11/2009 | Sendai |
| 2007/0076844 A1* | 4/2007 | Defreitas et al. ................ 378/37 |
| 2008/0247509 A1 | 10/2008 | Kashiwagi |

FOREIGN PATENT DOCUMENTS

| JP | 2007-125367 A | 5/2007 |
| JP | 2007289640 A | 11/2007 |
| WO | WO 2006058160 A2 * | 6/2006 |
| WO | 2009/068732 A1 | 6/2009 |

OTHER PUBLICATIONS

Communication, dated Oct. 14, 2010, issued in corresponding EP Application No. 10170577.0, 8 pages.
Rejection of the Application, dated Apr. 9, 2013, issued in corresponding JP Application No. 2009-172740, 4 pages in English and Japanese.

* cited by examiner

*Primary Examiner* — Ruth S Smith
(74) *Attorney, Agent, or Firm* — Sughrue Mion, PLLC

(57) ABSTRACT

In a radiographic image capturing apparatus, an object to be examined is compressed and secured between a compression plate and an image capturing base, at a position off-center from a central position of the image capturing base near a subject in a direction along the subject. An opening is defined in the compression plate so as to confront the object to be examined in the off-center position. The radiation source irradiates the object to be examined as well as the opening with radiation from a central angle of the radiation source, which is aligned with a vertical axis of the image capturing base, and which passes through the central position from a predetermined angle that is angularly spaced from the central angle about the central position.

5 Claims, 20 Drawing Sheets

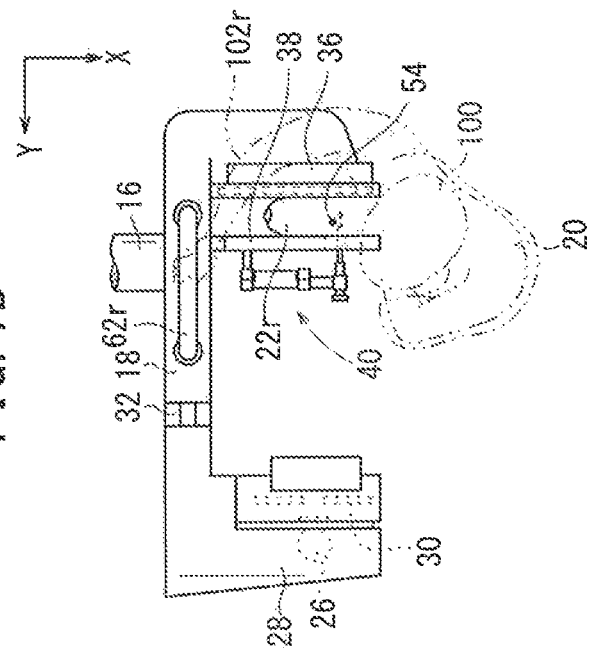
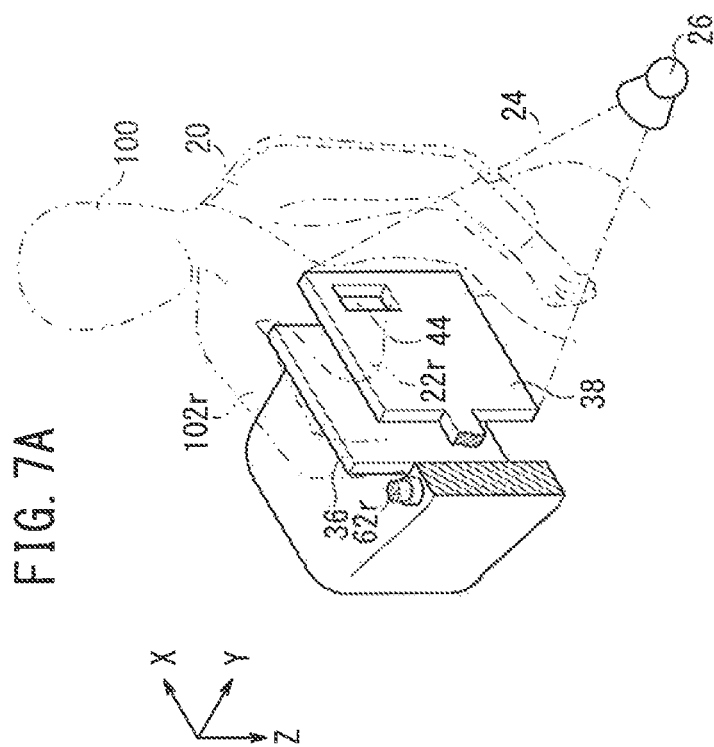
FIG. 7A
FIG. 7B

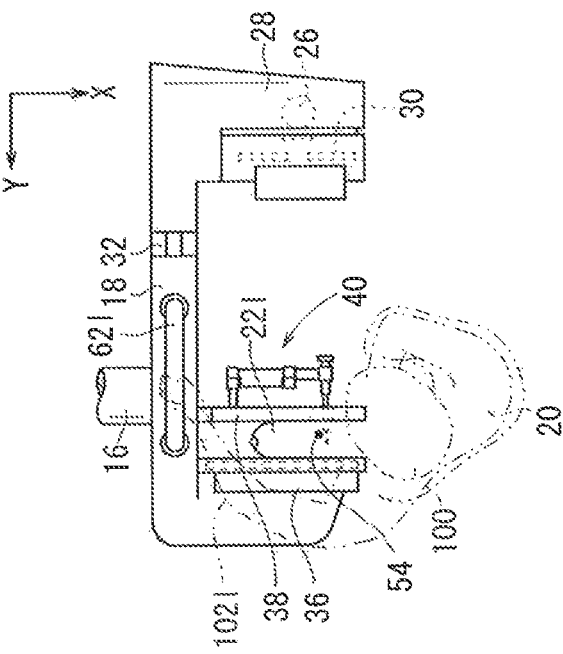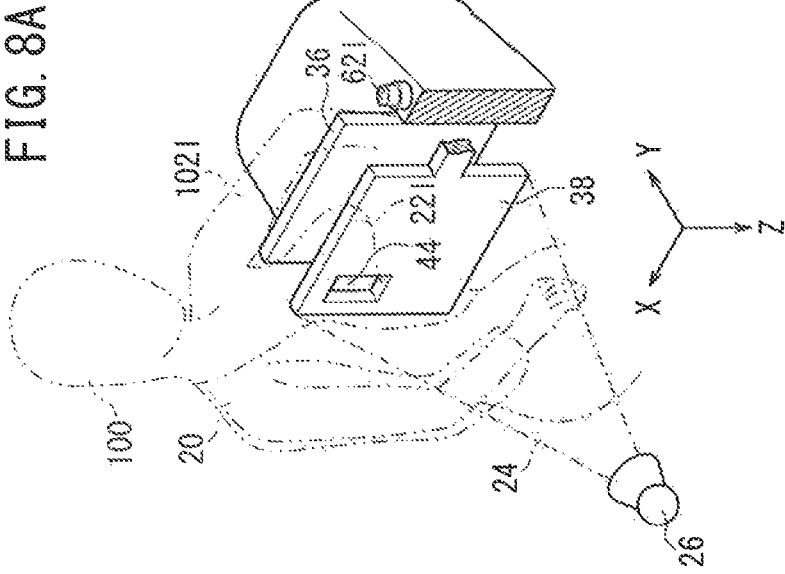

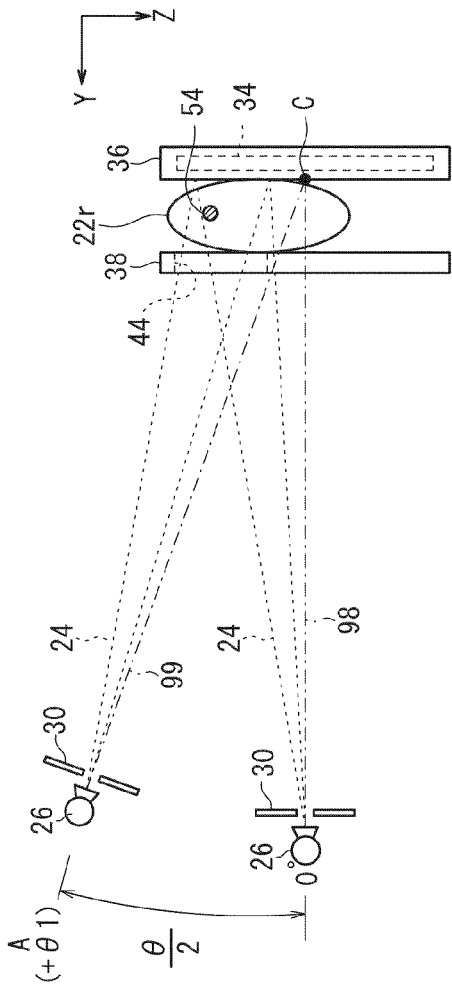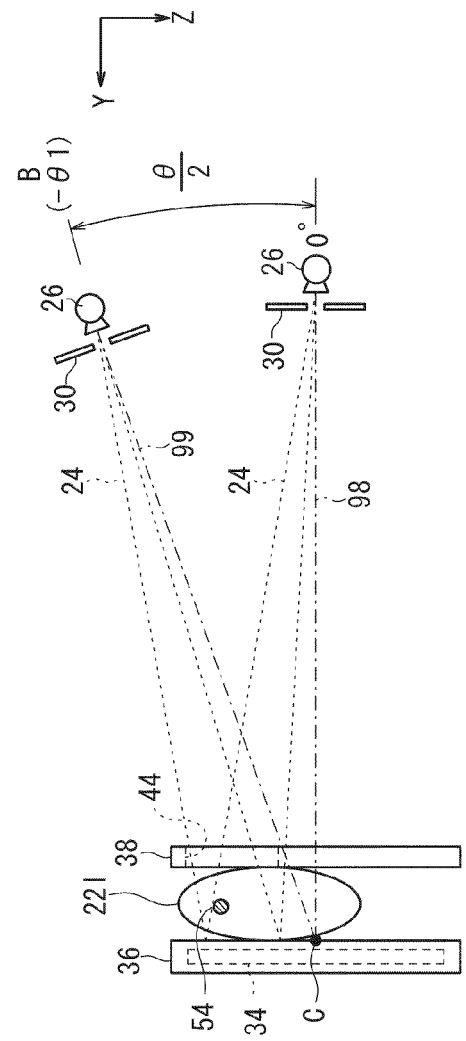
FIG. 9A
FIG. 9B

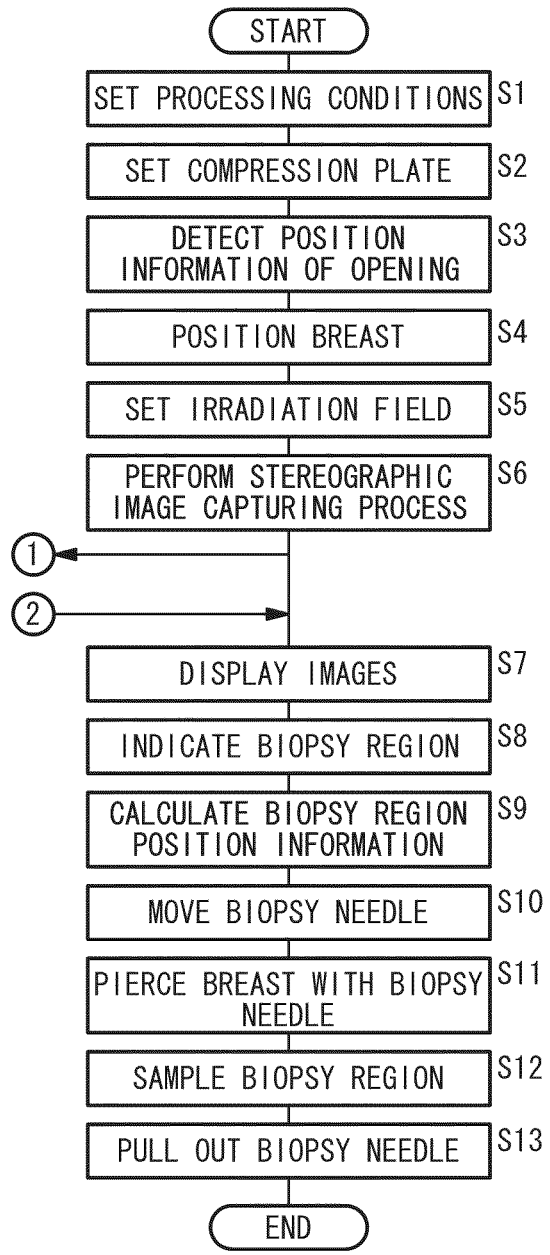

RADIOGRAPHIC IMAGE CAPTURING APPARATUS

CROSS-REFERENCE TO RELATED APPLICATION

This application is based upon and claims the benefit of priority from Japanese Patent Application No. 2009-172740 filed on Jul. 24, 2009, of which the contents are incorporated herein by reference.

BACKGROUND OF THE INVENTION

1. Field of the Invention

The present invention relates to a radiographic image capturing apparatus for compressing and securing an object to be examined of a subject between an image capturing base and a compression plate, then irradiating the object to be examined with radiation, and converting the radiation that has passed through the object to be examined into a radiographic image.

2. Description of the Related Art

There have heretofore been developed biopsy apparatus for sampling tissue of a biopsy region (e.g., a lesion region in a subject's breast) contained within an object to be examined of the subject, and thoroughly examining the sampled tissue to perform a disease diagnosis.

Such a biopsy apparatus is incorporated in a radiographic image capturing apparatus for capturing radiographic images of the object to be examined. The radiographic image capturing apparatus, with the biopsy apparatus incorporated therein, operates as follows. First, an object to be examined of a subject is compressed between an image capturing base and a compression plate, and the object is irradiated with radiation. Radiation that has passed through the object to be examined is converted into a radiographic image by a radiation detector, which is housed in the image capturing base. Based on the radiographic image, the position of a biopsy region in the object to be examined is calculated. Then, based on the calculated position of the biopsy region, a biopsy needle is passed through an opening provided in the compression plate in order to pierce the biopsy region, whereupon a tissue sample of the biopsy region is removed.

The opening is relatively small, e.g., the opening is a rectangular opening having a size of 5 cm×5 cm, which is just large enough to allow the biopsy needle to pass therethrough in order to remove a tissue sample of the biopsy region, but also is small enough to allow the compression plate to reliably compress the object to be examined. A region of the object to be examined, which faces the opening, serves as an examinable region from which the tissue sample can be removed. A region of the radiation detector, which is irradiated with radiation that has passed through the examinable region, serves as a radiation detecting region (image capturing region), which converts the radiation into a radiographic image corresponding to the examinable region.

Known forms of radiation detectors include a conventional radiation film for recording a radiographic image by exposure to radiation, and a stimulable phosphor panel for storing radiation energy representing the radiographic image in a phosphor, and thereafter reproducing the radiographic image as stimulated light by applying stimulating light to the phosphor. The radiation film, with the radiographic image recorded therein, is supplied to a developing device in order to develop the radiographic image. Alternatively, the stimulable phosphor panel is supplied to a reading device in order to read the radiographic image as a visible image.

In recent years, direct-conversion-type radiation detectors have been developed for directly converting radiation into electric signals, or indirect-conversion-type radiation detectors, which comprise a scintillator for temporarily converting radiation into visible light together with solid-state detectors that convert the visible light into electric signals in order to read the detected radiation image information. Such radiation detectors are widely used as radiation detectors for use in radiographic image capturing apparatus, because they are capable of shortening the time period required after the radiographic image of a subject has been captured and until the captured radiographic image is confirmed by a doctor or radiological technician.

Radiographic image capturing apparatus, which incorporate biopsy apparatus according to the related art, employ a CCD (Charge-Coupled Device) image sensor therein for reading an electric signal (electric charges), because the examinable region to be handled is very small, and the radiation detector that is used should be of a small size in order to match the examinable region. These radiographic image capturing apparatus are called SFDM (Small Field Digital Mammography) radiographic image capturing apparatus (mammographic image capturing apparatus).

It is a general practice to capture an image of an object to be examined as a CC (CranioCaudal) view by irradiating the subject to be examined, who is in a seated position, with radiation emitted from a radiation source positioned above the subject. In such an image capturing mode, the examinable region and the radiation detecting region are set near a central position on the image capturing base close to the subject. Further, the object to be examined is placed over the central position on the image capturing base, and the object is compressed and secured from above by the compression plate. The radiation source has a central angle set on a vertical axis of the image capturing base, which passes through the central position. The object to be examined, the central position, and the central angle are fixed to or set on the vertical axis.

To capture stereographic images as CC views, the radiation source is turned about a central position to assume predetermined angles (+θ1 and −θ1 in FIG. 4 of the accompanying drawings) from the central angle. When the radiation source is positioned at such angles, which are symmetrical with respect to the subject, the radiation source applies radiation to the object to be examined. When the radiation source is turned from the central angle (the aforementioned vertical axis), the radiation source possibly may come into contact with the head of the subject. In order to prevent the radiation source from contacting the head of the subject, the head of the subject needs to be spaced from the radiation source while stereographic images of the object to the examined are captured (see FIG. 5 of the accompanying drawings). During the stereographic image capturing process, therefore, and while tissue is being sampled from the object to be examined by a biopsy needle, the subject is required to keep her head uncomfortably tilted for a long period of time, e.g., from 30 minutes to 40 minutes.

In recent years, radiographic image capturing apparatus have become available on the market, which employ a direct-conversion-type radiation detector or an indirect-conversion-type radiation detector, as described above. Radiation detectors for use in such radiographic image capturing apparatus have a relatively large radiation detecting region, having a size of 18 cm×24 cm or 24 cm×30 cm, for example. Such radiographic image capturing apparatus are referred to as FFDM (Full Field Digital Mammography) radiographic image capturing apparatus, having a large examinable region and a large radiation detecting region. However, since the region of an object to be examined, which corresponds to an opening defined in the compression plate, serves as an examinable region, the examinable region of the object to be examined by the FFDM radiographic image capturing apparatus still remains relatively small.

Technologies concerning radiographic image capturing apparatus (mammographic image capturing apparatus) for capturing radiographic images of breasts, which define objects to be examined, are disclosed in Japanese Laid-Open Patent Publication No. 2007-125367 and U.S. Pat. No. 7,443,949. In Japanese Laid-Open Patent publication No. 2007-125367, it has been proposed to change relative positions of a radiation source and an image capturing base in a direction along the subject, depending on the size of the breast and the direction in which a radiographic image thereof is to be captured. In U.S. Pat. No. 7,443,949, a compression plate is proposed, which is movable in a direction along the subject.

In the radiographic image capturing apparatus according to the related art, as described above, the object to be examined is compressed and secured at a central position on the image capturing base close to the subject, and the vertical axis of the image capturing base, which passes through the central position, is set as the central axis of the radiation source. Accordingly, the central position, the object to be examined, and the central angle are fixed to or set on the same vertical axis. Consequently, the subject is required to assume an uncomfortable attitude in order to avoid obstructing the radiation source, which is turned symmetrically (equally) to the left and right with respect to the subject.

According to the technology disclosed in Japanese Laid-Open Patent Publication No. 2007-125367, when relative positions of the radiation source and the image capturing base are changed along the subject depending on the size of the breast and the direction in which the radiographic image thereof is captured, the object to be examined is off-center a given distance on the image capturing base from the central position in a direction along the subject. Further, the radiation source also is off-center a given distance from the vertical axis, in the same direction along the subject as the direction in which the object to be examined is off-center. Therefore, after the object to be examined and the radiation source have been off-center, the object to be examined and the central angle are made coaxial with each other. During the process of capturing stereographic images, the subject also is required to assume an uncomfortable attitude in order to avoid obstructing the radiation source, which is turned symmetrically (equally) to the left and right with respect to the subject.

According to the technology disclosed in U.S. Pat. No. 7,443,949, the compression plate is moved depending on the direction in which the object to be examined is imaged. However, there is nothing proposed in this technology concerning ways for allowing the subject to maintain a comfortable attitude, while radiographic images of an object to be examined are captured and tissue is sampled from a biopsy region in the object of examination.

SUMMARY OF THE INVENTION

It is an object of the present invention to provide a radiographic image capturing apparatus, which allows a subject to maintain a comfortable attitude while radiographic images of an object to be examined are captured and tissue is sampled from a biopsy region in the object of examination.

To achieve the above object, there is provided in accordance with the present invention a radiographic image capturing apparatus comprising a radiation source for applying radiation to an object to be examined of a subject, a radiation detector for detecting radiation that has passed through the object to be examined, and for converting the detected radiation into a radiographic image, an image capturing base housing the radiation detector therein, and a compression plate, which is displaceable toward the image capturing base to compress and secure the object to be examined on the image capturing base, wherein the object to be examined is compressed and secured between the compression plate and the image capturing base at a position off-center from a central position of the image capturing base near the subject in a direction along the subject, and wherein the radiation source irradiates the object to be examined with radiation from a central angle of the radiation source and from a predetermined angle that is angularly spaced from the central angle about the central position, the central angle being aligned with a vertical axis of the image capturing base, and the vertical axis passing through the central position.

According to the present invention, while the object to be examined is off-center from the central position of the image capturing base near the subject in the direction along the subject, the object to be examined is compressed and secured between the compression plate and the image capturing base. More specifically, the central angle of the radiation source and the central position of the image capturing base are aligned with the vertical axis, and only the object to be examined is positionally displaced (off-center) from the vertical axis in a direction along the subject. The object to be examined then is compressed and secured in position.

Since the position of the subject with respect to the radiographic image capturing apparatus also is off-center, when the radiation source is turned from the central angle about the central position, the radiation source is prevented from coming into contact with the subject, who remains in a natural attitude in a sitting position. As a result, the subject can remain at a natural attitude while an image capturing process is performed on the subject.

Since an examinable region and a radiation detecting region are changed when the object to be examined is displaced (off-center) from the central position in the direction along the subject, the examinable region and the radiation detecting region are enlarged virtually in order to increase the efficiency with which radiographic images are captured using the radiographic image capturing apparatus, particularly, an FFDM radiographic image capturing apparatus.

The radiographic image capturing apparatus preferably further comprises a region-of-interest position information calculator for calculating a three-dimensional position of a region of interest in the object to be examined, based on two radiographic images generated by the radiation detector in case that the radiation source irradiates the object to be examined with radiation from at least two angles.

With the above arrangement, the three-dimensional position of the region of interest can easily be calculated from two radiographic images, which are generated by a stereographic image capturing process. Furthermore, as described above, when the radiation source is turned about the central position from the central angle, the radiation source is prevented from coming into contact with the subject, who remains in a natural attitude in the sitting position. Therefore, the stereographic image capturing process can be carried out reliably.

The radiographic image capturing apparatus preferably further comprises a radiation source energization controller for controlling the radiation source in order to irradiate the object to be examined with radiation from the central angle as well as from the predetermined angle.

Since the radiation source is turned to unequal positions to the right and to the left of the subject during the stereographic image capturing process, unlike the stereographic image capturing process according to the related art, wherein the radiation source is turned to equal positions to the right and to the left, the radiation source and the subject are reliably prevented from coming into contact with each other. Therefore, radiographic images can be captured of the object to be examined without requiring the subject to be forced into an uncomfortable attitude.

The radiographic image capturing apparatus preferably further comprises an off-center position detector for detecting an off-center position of the object to be examined, and a collimator for controlling an irradiation field of the radiation such that at least a portion of the object to be examined is included within the irradiation field, based on the off-center position of the object to be examined that is detected by the off-center position detector.

With the above arrangement, since the irradiation field of the radiation, which is controlled depending on the off-center position of the object to be examined, radiographic images can be captured of the object to be examined including the region of interest.

In case that the radiation source irradiates the object to be examined with radiation in a lateral view capturing method, while the radiation source, the compression plate, and the image capturing base are arrayed substantially in a horizontal direction, the object to be examined preferably is compressed and secured between the compression plate and the image capturing base at a position that is off-center upwardly from the central position of the image capturing base near the subject.

Since the radiation source, the compression plate, and the image capturing base are arrayed substantially in a horizontal direction, the radiation source and the subject are reliably prevented from coming into contact with each other when the radiation source is turned from the central angle about the central position. Therefore, the subject can assume a natural attitude while a lateral view capturing method, such as an ML (MedioLateral) or an LM (LateroMedial) view capturing method, is carried out on the subject.

Furthermore, since the object to be examined is compressed and secured at a position off-center upwardly from the central position of the image capturing base near the subject, the subject can place her arm above the image capturing base. The subject therefore can assume a comfortable attitude while the lateral view capturing method is carried out.

The object to be examined preferably comprises a breast of the subject, whereas the radiographic image capturing apparatus preferably comprises a mammographic image capturing apparatus for applying radiation from the radiation source to the breast, while the breast is compressed and secured on the image capturing base by the compression plate, which is displaced toward the image capturing base along the vertical axis.

The radiographic image capturing apparatus preferably comprises an SFDM mammographic image capturing apparatus for setting a portion of the breast as an examinable region, detecting radiation that has passed through the examinable region with the radiation detector, and converting the detected radiation into the radiographic image, and the radiographic image capturing apparatus further includes a detector controller for moving the radiation detector to an area of the image capturing base that corresponds to the examinable region.

Therefore, the subject can assume a comfortable attitude, even when the subject is imaged by an SFDM mammographic apparatus. Since the radiation detector is moved within the image capturing base by the detector controller, radiographic images of the object to be examined can be captured efficiently.

The compression plate preferably has an opening defined therein at a position that confronts a biopsy region of the object to be examined. The radiographic image capturing apparatus preferably further comprises a biopsy needle capable of passing through the opening, piercing the biopsy region, and removing a tissue sample from the biopsy region based on the radiographic image, wherein the radiation source applies radiation to the object to be examined and the opening.

The opening is defined in the compression plate at a position that confronts the position of the off-center object to be examined. In other words, the opening also is displaced (off-center) to a position that corresponds to the position of the object to be examined, which is displaced from the vertical axis in the direction along the subject.

The subject therefore is kept at a natural attitude while radiographic images are captured of the object to be examined, and while a tissue sample is removed from the biopsy region. Since the examinable region of the biopsy region is changed when the opening is displaced (off-center) in the direction along the subject, the examinable region is enlarged virtually in order to increase the efficiency with which the biopsy region can be examined.

The opening may be defined in the compression plate at a position corresponding to the examinable region, or may be defined in a compression panel as a hole having a size corresponding to the examine region, such that the compression panel is inserted removably in a frame. In this manner, if the opening is defined in the compression panel, then the compression panel may be turned upside down or inverted horizontally, depending on the way in which the object to be examined is off-center on the image capturing base. Thereafter, the compression panel may be inserted into the frame so as to displace the opening (to be off-center).

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIGS. 7A and 7B are perspective and plan views, respectively, showing the manner in which a characteristic function of the present embodiment, which solves the problems illustrated in FIGS. 5 and 6, is applied during the process for capturing an ML view;

FIGS. 8A and 8B are perspective and plan views, respectively, showing the manner in which the characteristic function of the present embodiment, which solves the problems illustrated in FIGS. 5 and 6, is applied during the process for capturing an LM view;

FIG. 9A is a schematic view illustrating a stereographic image capturing process for capturing an ML view, as shown in FIGS. 7A and 7B;

FIG. 9B is a schematic view illustrating a stereographic image capturing process for capturing an LM view, as shown in FIGS. 8A and 8B;

FIG. 10 is a flowchart of an operation sequence of the mammographic apparatus shown in FIG. 3;

DESCRIPTION OF THE PREFERRED EMBODIMENTS

Figure 1:
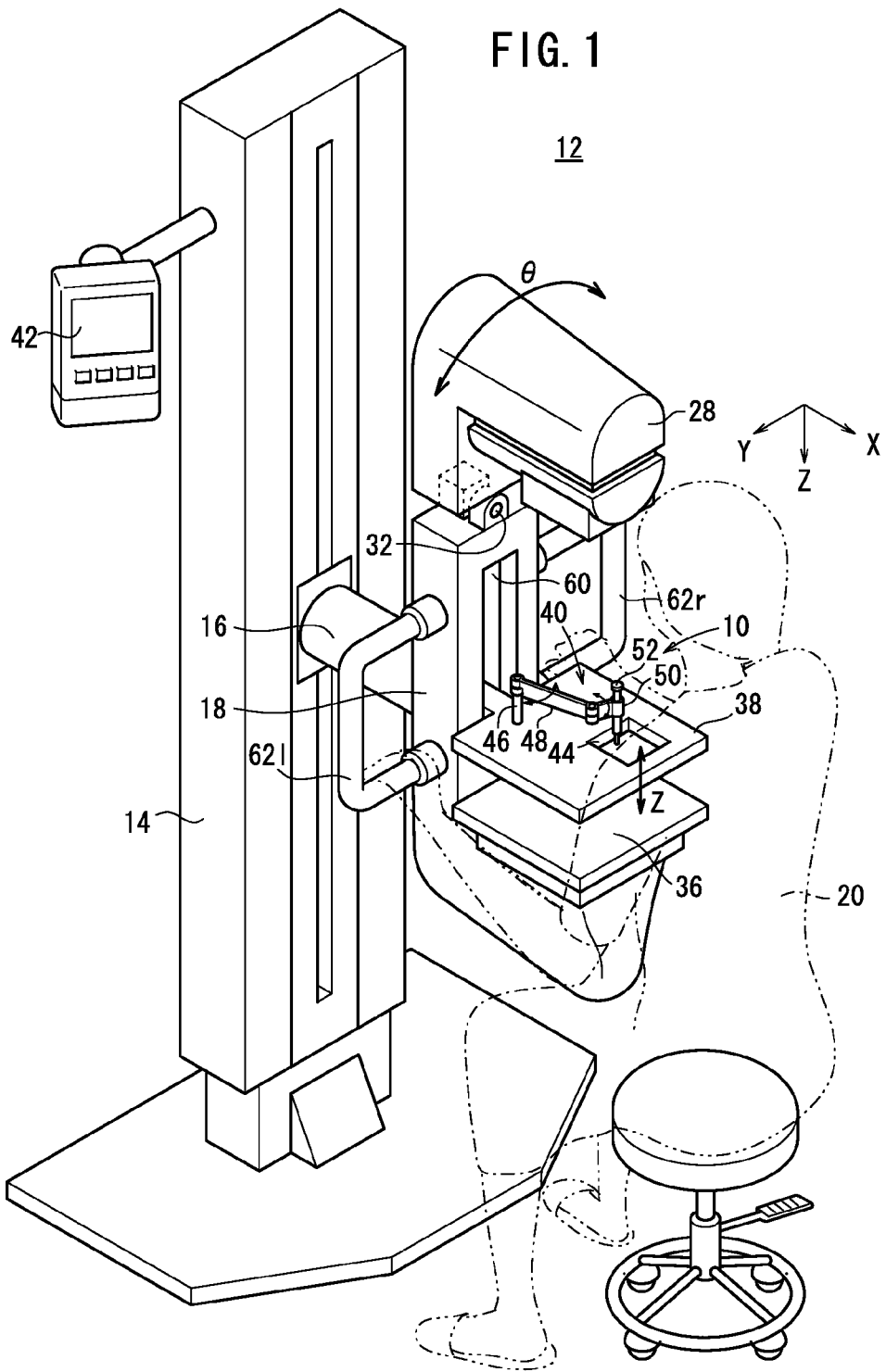
FIG. 1 is a perspective view of a mammographic apparatus that forms a radiographic image capturing apparatus according to an embodiment of the present invention.

A radiographic image capturing apparatus according to a preferred embodiment of the present invention will be described below with reference to the accompanying drawings.

The basic structure of a mammographic apparatus (radiographic image capturing apparatus, mammographic image capturing apparatus) 12 according to an embodiment of the present invention, which incorporates a biopsy apparatus therein, will be described below with reference to FIGS. 1 through 3.

The mammographic apparatus 12 essentially includes an upstanding base 14, a vertical arm 18 fixed to the distal end of a swing shaft 16 disposed substantially centrally on the base 14, a radiation source housing unit 28 fixed to an upper end of the arm 18 and housing therein a radiation source 26 for applying radiation 24 to a breast 22 (22r, 22l), which defines a mass to be examined of an examinee (subject) 20, an image capturing base 36 mounted on a lower end of the arm 18 and housing therein a solid-state detector (radiation detector) 34 for detecting radiation 24 that has passed through the breast 22, a compression plate 38 for compressing and holding the breast 22 against the image capturing base 36, and a biopsy hand assembly (biopsy needle moving mechanism) 40 mounted on the compression plate 38 for removing a tissue sample from a biopsy region (region of interest) 54 of the breast 22.

Figure 2:
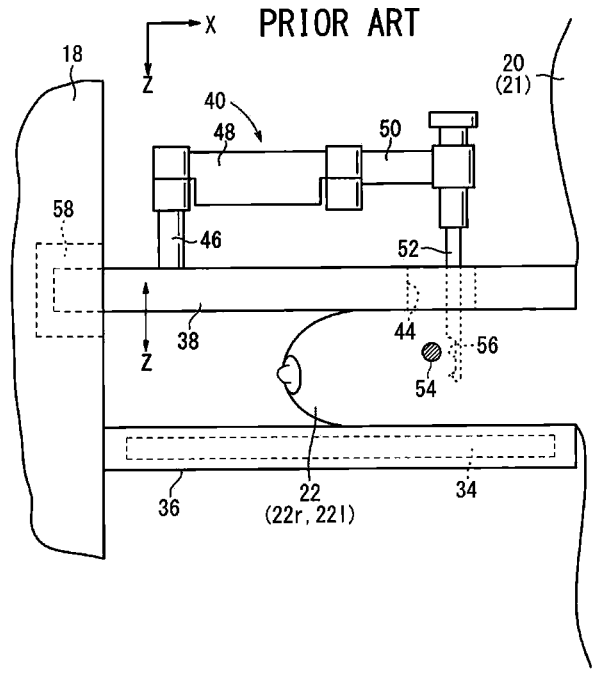
FIG. 2 is an enlarged fragmentary side elevational view of the mammographic apparatus shown in FIG. 1.
Figure 3:
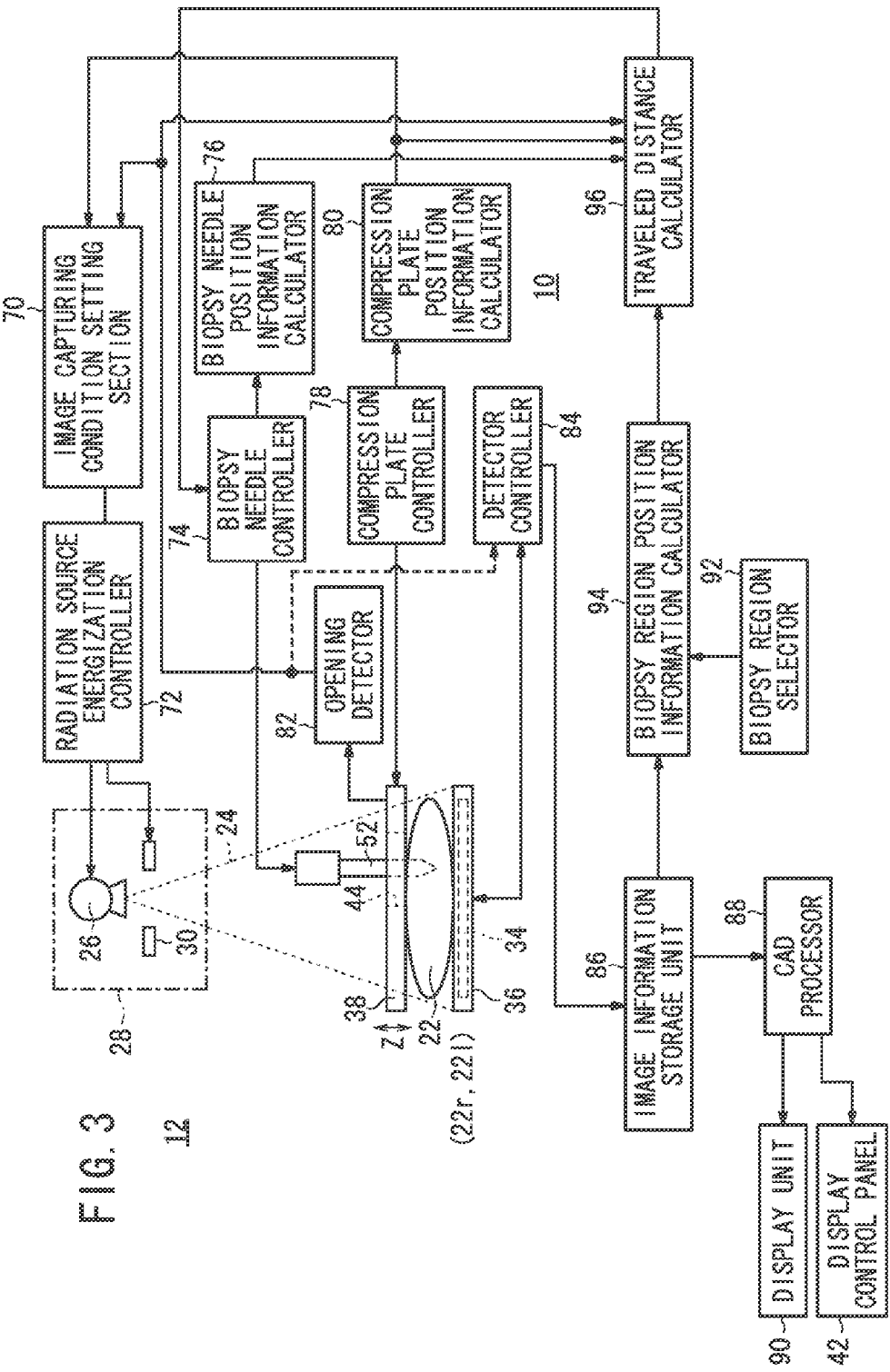
FIG. 3 is a block diagram of the mammographic apparatus shown in FIG. 1.

In FIGS. 1 through 3, the mammographic apparatus 12 applies radiation 24 to the breast 22 of the examinee 20 in order to capture a CC view of the breast 22 and a sample tissue is removed from the biopsy region 54, while the breast 22 of the examinee 20, who is in a sitting position, is compressed and secured between the compression plate 38 and the image capturing base 36. A display control panel 42 is connected to the base 14 for displaying image capturing conditions representing an image capturing region of the examinee 20, ID information of the examinee 20, etc., and for enabling setting of such items of information, if necessary. The radiation source housing unit 28 also houses therein a collimator 30 for delimiting an irradiated field of radiation 24 that is emitted from the radiation source 26.

As shown in FIG. 2, the solid-state detector 34 housed in the image capturing base 36 has a depth, i.e. an X-direction length, which is slightly smaller than the depth of the image capturing base 36. Therefore, the mammographic apparatus 12 shown in FIGS. 1 and 2 is an FFDM apparatus type, having a relatively large radiation detecting region (image capturing region).

As shown in FIG. 1, when the arm 18, to which the radiation source housing unit 28 and the image capturing base 36 are secured, is angularly moved about the swing shaft 16, the direction of the radiation source housing unit 28 and the image capturing base 36 with respect to the breast 22 of the examinee 20 can be adjusted. The radiation source housing unit 28 is operatively coupled to the arm 18 by a hinge 32, and can be turned about the hinge 32 in directions indicated by the arrow θ independently of the image capturing base 36.

The arm 18 has a groove 60 defined vertically in a side (front side) thereof, which faces toward the examinee 20 in the direction indicated by the arrow X. The groove 60 extends along the direction indicated by the arrow Z. Handles 62r, 62l are mounted on respective sides of the arm 18, which face away from each other along the direction indicated by the arrow Y. The handles 62r, 62l may be gripped by the examinee 20. As shown in FIGS. 1 and 2, the compression plate 38 has a proximal end inserted into the groove 60 and held in interfitting engagement with a mount 58 disposed in the arm 18. The compression plate 38, which is thus coupled to the arm 18, is disposed between the radiation source housing unit 28 and the image capturing base 36. The compression plate 38 is vertically displaceable in unison with the mount 58 along the arm 18 in directions indicated by the arrow Z, when the mount 58 similarly is displaced in directions indicated by the arrow Z along the groove 60.

The compression plate 38 has an opening 44 defined therein near a chest wall 21 (see FIG. 2) of the examinee 20, for allowing the biopsy hand assembly 40 to remove a tissue sample from the biopsy region 54 of the breast 22. The biopsy hand assembly 40 makes up part of a biopsy apparatus 10 (see FIG. 3), which is incorporated in the mammographic apparatus 12. The biopsy hand assembly 40 comprises a post 46 fixedly mounted on the compression plate 38, a first arm 48 having one end thereof pivotally supported on the post 46, and which is angularly movable about the post 46 along the surface of the compression plate 38, and a second arm 50 having one end thereof pivotally supported on another end of the first arm 48, and which is angularly movable about the other end of the first arm 48 along the surface of the compression plate 38. A biopsy needle 52 is mounted on the other end of the second arm 50 for movement in directions indicated by the arrow Z perpendicular to the compression plate 38.

As shown in FIG. 2, the biopsy needle 52 has a sampler 56 disposed near the lower end thereof, for sampling under suction a tissue (e.g., calcified tissue) from the biopsy region 54, which forms a lesion area (e.g., calcified area) of the breast 22. The sampler 56 of the biopsy needle 52 can be moved to a position in the vicinity of the biopsy region 54 when the first arm 48 and the second arm 50 of the biopsy hand assembly 40 are moved in an X-Y plane parallel to the surface of the compression plate 38, and when the biopsy needle 52 is moved in directions indicated by the arrow Z.

FIG. 3 shows a block diagram of the mammographic apparatus 12, including the biopsy apparatus 10.

As shown in FIG. 3, the mammographic apparatus 12 includes an image capturing condition setting section 70, a radiation source energization controller 72, a biopsy needle controller 74, a biopsy needle position information calculator 76, a compression plate controller 78, a compression plate position information calculator 80, an opening detector (off-center position detector) 82, a detector controller 84, an image information storage unit 86, a CAD (Computer Aided Diagnosis) processor 88, a display unit 90, a biopsy region selector 92, a biopsy region position information calculator (region-of-interest position information calculator) 94, and a traveled distance calculator 96.

The biopsy hand assembly 40, the biopsy needle 52, the opening 44, the biopsy needle controller 74, the biopsy needle position information calculator 76, the opening detector 82, the biopsy region selector 92, and the traveled distance calculator 96 collectively make up the biopsy apparatus 10 for sampling a tissue of the biopsy region 54, and are incorporated in the mammographic apparatus 12.

The image capturing condition setting section 70 sets image capturing conditions including a tube current and a tube voltage of the radiation source 26, target and filter types that are set in the radiation source 26, an irradiation dose and an irradiation time of the radiation 24, and an angle of the radiation source 26 with respect to the vertical axis (see FIGS. 4, 9A, and 9B) of the image capturing base 36 in a stereographic image capturing process, etc. The radiation source energization controller 72 controls energization of the radiation source 26 and the collimator 30 according to the image capturing conditions. The biopsy needle controller 74 controls the biopsy hand assembly 40 (see FIGS. 1 and 2) in order to move the biopsy needle 52 to a desired position. The compression plate controller 78 moves the mount 58 along the groove 60 in the directions indicated by the arrow Z, so as to move the compression plate 38 in unison with the mount 58 in the directions indicated by the arrow Z. The detector controller 84 controls the solid-state detector 34 in order to store a radiographic image, which is converted by the solid-state detector 34 from the radiation 24, in the image information storage unit 86.

The mammographic apparatus 12 is capable of performing a stereographic image capturing process for acquiring radiographic images of the breast 22 at two respective image capturing angles by turning the radiation source housing unit 28 about the hinge 32 (see FIG. 1), placing the radiation source 26 and the collimator 30 in two respective positions (two image capturing angles along the directions indicated by the arrow θ), and capturing radiographic images based on radiation 24 emitted from the radiation source 26, which is placed in two positions. In the stereographic image capturing process, more specifically, the radiation source housing unit 28 is turned about the hinge 32 in order to place the radiation source 26 and the collimator 30 at two image capturing angles (e.g., 0° and +θ1 in FIG. 9A, or −θ1 and 0° in FIG. 9B) one at a time. Then, the radiation source 26 applies radiation 24 to the breast 22, whereupon the radiation 24 passes through the breast 22 and contacts the solid-state detector 34, which converts the radiation 24 into radiographic images. Accordingly, the image information storage unit 86 stores two radiographic images of the breast 22 at two respective image capturing angles.

The CAD processor 88 processes the two radiographic images stored in the image information storage unit 86, and displays the processed radiographic images on the display unit 90 and the display control panel 42.

The biopsy region selector 92 comprises a pointing device such as a mouse or the like. Using the pointing device as the biopsy region selector 92, a doctor or radiological technician in charge, who has seen the displayed contents, i.e., the two radiographic images, on the display unit 90 and/or the display control panel 42, can select one out of a plurality of biopsy regions 54 displayed in the two radiographic images from which a tissue is to be removed. More specifically, the doctor or radiological technician selects a biopsy region 54 in one of the two radiographic images, and also selects a corresponding biopsy region 54 in the other of the two radiographic images.

The biopsy region position information calculator 94 calculates the three-dimensional position of the selected biopsy region 54 based on the positions of the selected biopsy region 54 in the two radiographic images. The three-dimensional position of the selected biopsy region 54 can be calculated according to a known three-dimensional position calculating scheme implemented in the stereographic image capturing process.

The biopsy needle position information calculator 76 calculates position information of the tip end of the biopsy needle 52, which has been moved by the biopsy needle controller 74. When a tissue is sampled from the biopsy region 54, the biopsy needle position information calculator 76 calculates the position of the tip end of the biopsy needle 52 before tissue is sampled from the biopsy region 54. Stated otherwise, the position of the tip end of the biopsy needle 52 is calculated before the biopsy needle 52 pierces the breast 22.

The opening detector 82 detects the position of the opening 44 in the compression plate 38, the proximal end of which is held in interfitting engagement with the mount 58. The opening detector 82 may comprise a bar-code reader. For example, a bar code, which stores information concerning the compression plate 38 including the position information of the opening 44 therein, may be applied to the proximal end of the compression plate 38. Then, when the proximal end of the compression plate 38 is brought into interfitting engagement with the mount 58, the bar code may be read by a bar-code reader, which is combined with the mount 58, in order to detect the position of the opening 44. The position of the opening 44 may alternatively be detected by any of various other means.

As shown in FIG. 2, since the breast 22 is compressed and secured in alignment with the opening 44, the position information of the opening 44, which is detected by the opening detector 82, also is representative of the position of the breast 22 that is compressed and secured on the image capturing base 36.

In FIG. 3, the compression plate position information calculator 80 calculates position information of the compression plate 38, which has been moved with respect to the image capturing base 36 by the compression plate controller 78. Since the compression plate 38 presses against the breast 22 with respect to the image capturing base 36 and holds the breast 22 in a pressed state, the position information of the compression plate 38 represents thickness information of the breast 22 as the breast 22 is being pressed.

The traveled distance calculator 96 calculates the distance by which the biopsy needle 52 is moved with respect to the biopsy region 54, based on the three-dimensional position of the biopsy region 54, which has been calculated by the biopsy region position information calculator 94, the position of the tip end of the biopsy needle 52, which has been calculated by the biopsy needle position information calculator 76, the position of the opening 44, which has been detected by the opening detector 82, and the position of the compression plate 38, which has been calculated by the compression plate position information calculator 80 (i.e., the thickness of the breast 22). Based on the calculated distance that the biopsy needle 52 is moved with respect to the biopsy region 54, the biopsy needle controller 74 moves the biopsy needle 52 in order to enable a tissue sample from the selected biopsy region 54 to be removed.

The image capturing condition setting section 70 also sets the position information of the compression plate 38, which is calculated by the compression plate position information calculator 80, and the position information of the opening 44, which is detected by the opening detector 82. The collimator 30 controls the irradiated field of radiation 24, such that the opening 44 and a portion of the breast 22 (a portion including the biopsy region 54) fall within the irradiated field. A region of the solid-state detector 34, which is irradiated by radiation 24, serves as an image capturing region (radiation detecting region). A radiographic image output from the solid-state detector 34 is converted from the radiation 24 applied to the image capturing region.

Since the biopsy needle 52 is moved vertically in directions indicated by the arrow Z by the biopsy hand assembly 40, the size of the opening 44 represents a range within which the biopsy needle 52 can pierce the breast 22. Therefore, a region of the breast 22, which corresponds to the opening 44 along the directions indicated by the arrow Z, serves as an examinable region, from which a tissue sample can be removed from the biopsy region 54 by the biopsy needle 52.

The mammographic apparatus 12 according to the embodiment of the present invention basically is constructed as described above.

Problems solved by the mammographic apparatus 12 according to the present embodiment will be described below with reference to FIGS. 4 through 6. Components shown in FIGS. 4 through 6 which are identical to those shown in FIGS. 1 through 3 will be denoted by identical reference characters.

Figure 4:
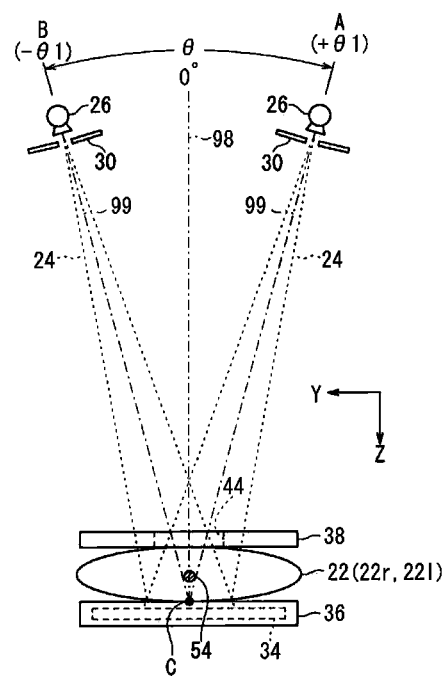
FIG. 4 is a schematic view illustrating a stereographic image capturing process for capturing a CC view according to the related art.

FIG. 4 is a schematic view illustrating a stereographic image capturing process for capturing a CC view according to the related art.

Figure 5:
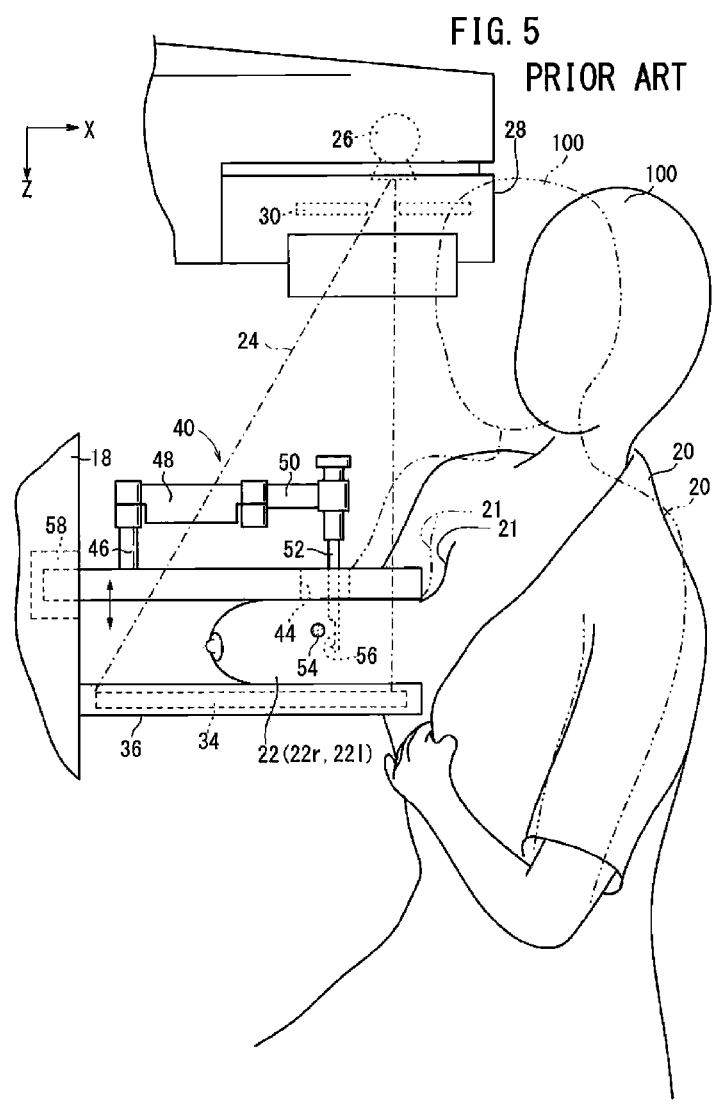
FIG. 5 is a fragmentary side elevational view illustrating problems that occur in the process for capturing a CC view.

In FIGS. 4 and 5, a vertical axis 98 of the image capturing base 36, which passes through a central position C on the upper surface of the image capturing base 36 near the chest wall 21 of the examinee 20, is established as a central angle (0°) of the radiation source 26 and the collimator 30.

In the stereographic image capturing process according to the related art, the radiation source housing unit 28 is turned to the left and right of the examinee 20 by equal distances about the central position C in the directions indicated by the arrow θ, thereby setting the radiation source 26 at equal image capturing angles to the left and right of the examinee 20. Then, the radiation source 26, having been set at the image capturing angles, applies radiation 24 one at a time to the breast 22 in order to capture a stereographic image thereof.

More specifically, the radiation source housing unit 28 is turned about the central position C through an angle +θ1 (e.g., +θ1=+15°) in order to place the radiation source 26 and the collimator 30 at the position A. Then, the radiation source housing unit 28 is turned about the central position C through an angle −θ1 (e.g., −θ1=−15°) in order to place the radiation source 26 and the collimator 30 at the position B.

Central axes 99 interconnect the radiation source 26, which is placed in positions A and B, and the central position C. The radiation source 26, having been placed in positions A and B, applies radiation 24 to the breast 22 along the central axes 99.

In FIGS. 4 and 5, the breast 22 is compressed and secured on the vertical axis 98 that passes through the central position C, and the central angle of the radiation source 26 is established on the vertical axis 98. Therefore, the central position C, the breast 22, and the central angle of the radiation source 26 are held in coaxial alignment with each other along the vertical axis 98.

According to the related art, in order to perform a stereographic image capturing process on the breast 22 to capture a CC image thereof, when the radiation source 26 and the collimator 30 are turned about a central position C symmetrically (equally) with respect to the position A through the angle +θ1 (e.g., +θ1=+15°) and the position B through the angle −θ1 (e.g., −θ1=−15°), the radiation source housing unit 28, which houses the radiation source 26 and the collimator 30 therein, tends to come into contact with the head 100 of the examinee 20. Therefore, the head 100 of the examinee 20 must be spaced a certain distance from the radiation source housing unit 28, which is turned equally to the left and right during the stereographic image capturing process.

More specifically, the examinee 20 is required to assume an improper and uncomfortable attitude by spacing her head 100 a significant distance away from the radiation source housing unit 28 in the direction indicated by the arrow X for a long period of time, e.g., for 30 minutes to 40 minutes, while the stereographic image capturing process is carried out, and also while tissue is being removed by the biopsy needle 52 from the biopsy region 54. Particularly, if the biopsy region 54 is located in an upper portion of the breast 22 or below the armpit, then the examinee 20 is required to remain in an unduly uncomfortable attitude.

In FIG. 5, the examinee 20 is shown as being in a natural attitude by the two-dot-dash lines. An examinee 20 in such a natural attitude is more likely to come into contact with the radiation source housing unit 28. In FIG. 5, the examinee 20 is shown as being in an improper attitude (i.e., an uncomfortable position) by the solid lines.

In order to capture radiographic images of the breast 22 and remove a tissue sample from the biopsy region 54 while the examinee 20 is allowed to remain in a comfortable attitude, rather than the above improper attitude discussed above, it is desirable to turn the arm 18 through 90° about the swing shaft 16, for thereby placing and aligning the radiation source housing unit 28, the compression plate 38, and the image capturing base 36 in an array along the directions indicated by the arrow Y. More specifically, after the breast 22 has been compressed and secured between the compression plate 38 and the image capturing base 36, radiation 24 is applied to the breast 22 from the radiation source 26 in order to capture a sideways radiographic image of the breast 22 (i.e., to capture an LM view or an ML view, as shown in FIG. 6). Thereafter, the biopsy needle 52 removes a tissue sample from the biopsy region 54.

Since the radiation source housing unit 28 is widely spaced from the head 100 when the arm 18 is turned 90° about the swing shaft 16, the head 100 of the examinee 20 and the radiation source housing unit 28 are less likely to come into contact with each other, even when the radiation source housing unit 28 is turned about the central position C in the directions indicated by the arrow θ, in a stereographic image capturing process for capturing an ML view or an LM view.

As shown in FIGS. 4 and 5, the opening 44 is defined centrally in the compression plate 38, near the chest wall 21 of the examinee 20. In FIG. 6, a natural attitude of the examinee 20 in the sitting position is indicated by the two-dot-and-dash lines. When the compression plate 38 is turned 90° upon swinging movement of the arm 18, the position of the opening 44 after having been turned is below the position of the breast 22r of the examinee 20, who is positioned in a natural attitude, in the direction indicated by the arrow Z. Consequently, for performing a stereographic image capturing process to capture an ML view, as well as to remove a tissue sample from the biopsy region 54, the examinee 20 has to assume an improper (uncomfortable) attitude (as indicated by the solid and broken lines in FIG. 6), in which the head 100 and the breast 22r of the examinee 20 are shifted downwardly.

Figure 6:
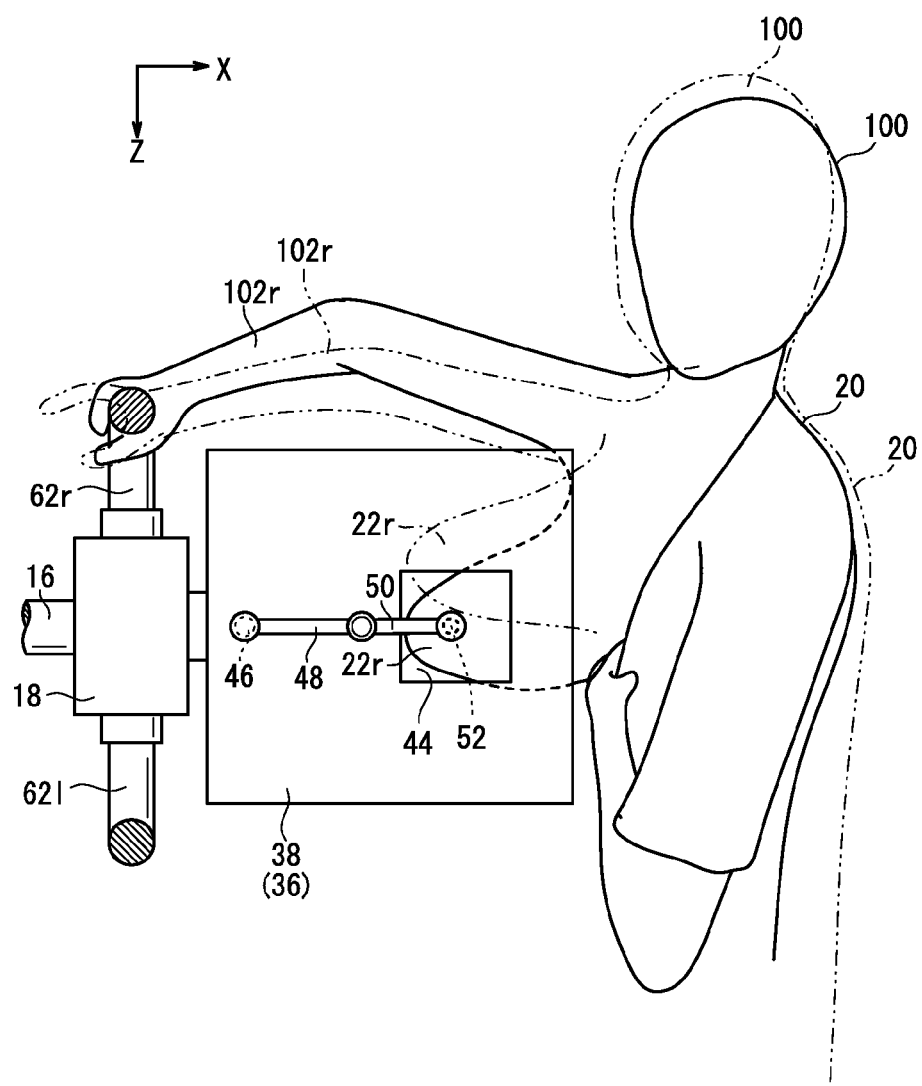
FIG. 6 is a fragmentary side elevational view illustrating problems that occur in a process for capturing an ML view.

When in a natural attitude, the examinee 20 can grip the handle 62r with the right arm 102r placed above the image capturing base 36 as shown in FIG. 6, and hence the examinee 20 stays relatively comfortable. However, in practice, since the examinee 20 needs to positionally align her breast 22r with the opening 44, the examinee 20 needs to maintain an improper attitude for a long period of time, with the elbow of the right arm 102r being lifted above the image capturing base 36.

In FIG. 6, the above problem has been described with respect to a process for capturing an ML view, in which the right breast 22r of the examinee 20 is compressed and secured between the compression plate 38 and the image capturing base 36. However, the same problem also occurs during a process of capturing an LM view, in which the left breast 22l of the examinee 20 is compressed and secured between the compression plate 38 and the image capturing base 36.

Characteristic functions of the mammographic apparatus 12 according to the present embodiment, which solve the problems shown and described above with reference to FIGS. 4 through 6, shall be described below with reference to FIGS. 7A through 9B.

According to the characteristic functions of the mammographic apparatus 12 according to the present embodiment, the central angle of the radiation source 26 and the central position C of the image capturing base 36 are aligned with the vertical axis 98. Also, the breast 22 (22r, 22l) and the opening 44 are off-center (displaced) in a direction along the chest wall 21 of the examinee 20, with respect to the chest wall 21. The radiation source 26 applies radiation 24 to the breast 22 and the opening 44 that have been off-center, and thereafter, a tissue sample is removed from the biopsy region 54.

More specifically, for capturing an ML view, as shown in FIGS. 7A, 7B and 9A, the central angle of the radiation source 26 and the central position C of the image capturing base 36 are aligned with the vertical axis 98, and the breast 22r is compressed and secured between the image capturing base 36 and the compression plate 38, at a position that is off-center upwardly (in the direction indicated by the arrow Z) with respect to the vertical axis 98. The opening 44 also is displaced to a position that is off-center upwardly with respect to the vertical axis 98, so as to confront the breast 22r. Therefore, a straight line, which interconnects the center of the off-center opening 44 and the position of the radiation source 26 at the central angle, is not perpendicular to the image capturing base 36.

For capturing an LM view, as shown in FIGS. 8A, 8B and 9B, the central angle of the radiation source 26 and the central position C of the image capturing base 36 are aligned with the vertical axis 98, and the breast 22l is compressed and secured between the image capturing base 36 and the compression plate 38 at a position that is off-center upwardly (in a direction indicated by the arrow Z) with respect to the vertical axis 98. The opening 44 also is displaced to a position that is off-center upwardly with respect to the vertical axis 98, so as to confront the breast 22l.

A comparison between FIGS. 7A, 8A, 9A, 9B and FIG. 6 indicates that the position of the off-center opening 44, as shown in FIGS. 7A, 8A, 9A and 9B, is aligned with the position of the breast 22 of the examinee 20, which is indicated by the two-and-dot-dash line shown in FIG. 6.

According to characteristic functions of the present embodiment shown in FIGS. 7A through 9B, the examinee 20 can assume a natural attitude by positioning her breasts 22r, 22l in alignment with the position of the off-center opening 44. When the breasts 22r, 22l off-center in this manner are compressed and secured between the image capturing base 36 and the compression plate 38, the examinee 20 remains comfortable and in a natural position while radiographic images are captured of the breasts 22r, 22l, as well as during removal of a tissue sample from the biopsy region 54.

The examinee 20 can grip the handles 62r, 62l with her arms 102r, 102l, which are positioned above the image capturing base 36 in an upward direction, as indicated by the arrow Z, while the examinee 20 remains in a natural attitude. Therefore, the examinee 20 remains comfortable and in a natural position while ML and LM radiographic images are captured of the breasts 22r, 22l, as well as during removal of a tissue sample from the biopsy region 54.

In FIGS. 7A through 9B, radiation 24 is applied to the breasts 22r, 22l when the radiation source 26 and the collimator 30 are held at image capturing angles of 0° and +θ1 (for capturing an ML view), or at image capturing angles of 0° and −θ1 (for capturing a LM view), respectively. In other words, as shown in FIGS. 7A through 9B, during the stereographic image capturing process, the radiation source housing unit 28 (made up of the radiation source 26 and the collimator 30) is turned to respective positions, which are asymmetrical to the right and the left (unequal to the right and the left) of the examinee 20, unlike the stereographic image capturing process shown in FIGS. 4 through 6. By turning the radiation source housing unit 28 in this manner, the examinee 20 and the radiation source housing unit 28 are reliably prevented from coming into contact with each other. Therefore, radiographic images can be captured of the breast 22r, 22l of the examinee 20, and a tissue sample can be removed from the biopsy region 54, without causing the examinee 20 to be forced into an improper (i.e., uncomfortable) attitude.

In FIG. 9A, the collimator 30 controls the irradiated field of radiation 24, such that the off-center opening 44 and a portion of the off-center breast 22r (a portion including the biopsy region 54) fall within the irradiated field. Similarly, in FIG. 9B, the collimator 30 controls the irradiated field of radiation 24, such that the off-center opening 44 and a portion of the off-center breast 22l (a portion including the biopsy region 54) fall within the irradiated field.

Characteristic functions of the mammographic apparatus 12 according to the present embodiment have been described above. Operations of the mammographic apparatus 12 shall now be described below with reference to the flowchart shown in FIG. 10. It is assumed that a stereographic image capturing process for capturing an ML view and an LM view is performed, and thereafter a tissue sample is removed from the biopsy region 54.

In step S1 in FIG. 10, the image capturing condition setting section 70 (see FIG. 3) sets image capturing conditions, including a tube current and a tube voltage of the radiation source 26, an irradiation dose and an irradiation time for the radiation 24, an image capturing method, an irradiation time for the radiation 24, an image capturing angle of the radiation source 26, etc., depending on conditions of the breast 22 (22r, 22l). The image capturing conditions are set in this manner in the radiation source energization controller 72.

In step S2, a doctor or radiological technician attaches the compression plate 38 to the mount 58, corresponding to the indicated image capturing method (an ML view capturing method or an LM view capturing method). In step S3, the opening detector 82 reads a bar code applied to the proximal end of the compression plate 38 with the bar-code reader, detects the position information of the opening 44 in the compression plate 38 from the read bar code information, and outputs the detected position information to both the image capturing condition setting section 70 and the traveled distance calculator 96.

In step S4, the swing shaft 16 is turned depending on the image capturing method in order to turn the arm 18 until the radiation source housing unit 28, the compression plate 38, and the image capturing base 36 are aligned in the direction indicated by the arrow Y (see FIGS. 7A through 9B). Then, the radiological technician positions the breast 22 of the examinee 20. More specifically, the radiological technician places the breast 22 in a predetermined position (facing the opening), which is off-center upwardly from the central position C of the image capturing base 36, and then energizes the compression plate controller 78 to move the compression plate 38 toward the image capturing base 36 in the direction indicated by the arrow Z, thereby compressing and positioning the breast 22 against the image capturing base 36.

The breast 22, which has been off-center upwardly from the central position C, is compressed and secured between the image capturing base 36 and the compression plate 38. If an ML view is to be captured, then the examinee 20 can grip the handle 62r with her arm 102r, which is placed above the image capturing base 36. Alternatively, if an LM view is to be captured, then the examinee 20 can grip the handle 62r with her arm 102l, which is placed above the image capturing base 36.

The compression plate position information calculator 80 calculates position information of the compression plate 38 with respect to the image capturing base 36, and outputs the calculated position information both to the image capturing condition setting section 70 and the traveled distance calculator 96.

In step S5, the image capturing condition setting section 70 sets the position information of the opening 44 from the opening detector 82, as well as the position information of the compression plate 38 from the compression plate position information calculator 80. Thereafter, the image capturing condition setting section 70 outputs the set position information to the radiation source energization controller 72. Based on the position information input from the image capturing condition setting section 70, and the image capturing conditions input from the image capturing condition setting section 70 in step S1, the radiation source energization controller 72 sets an irradiation field for the radiation 24, which is delimited (controlled) by the collimator 30.

After the above preparatory process for stereographic image capturing is completed, in step S6, the mammographic apparatus 12 energizes the radiation source 26 in order to perform a stereographic image capturing process on the breast 22. More specifically, the radiation source housing unit 28 is turned about the hinge 32 (see FIG. 1) to position the radiation source 26 successively at the central angle and the position A shown in FIG. 9A, or successively at the central angle and the position B shown in FIG. 9B. When the radiation source 26 is positioned successively at the central angle and the position A, or successively at the central angle and the position B, the radiation source 26 emits radiation 24, which passes through the breast 22 and is applied to the solid-state detector 34 in the image capturing base 36. Then, the solid-state detector 34 detects radiographic images of the breast 22 based on radiation 24 that is transmitted through the breast 22.

Since the collimator 30 controls the irradiation field of the radiation 24 according to a given irradiation field, which has been set by the radiation source energization controller 72 in step S5, the opening 44 and a portion of the breast 22 including the biopsy region 54 are reliably included within the irradiation field suitable for the stereographic image capturing process.

The detector controller 84 controls the solid-state detector 34 in order to acquire radiographic images of the breast 22, based on radiation 24 from the radiation source 26 in the central position and the position A for capturing an ML view, or in the central position and the position B for capturing an LM view, and the acquired two radiographic images are stored in the image information storage unit 86.

In step S7, the CAD processor 88 processes the two radiographic images stored in the image information storage unit 86, and displays the processed radiographic images on the display unit 90 and the display control panel 42.

In step S8, using the biopsy region selector 92, which is a pointing device such as a mouse, a doctor or radiological technician selects, from among a plurality of biopsy regions 54 in the two radiographic images displayed on the display unit 90 and/or on the display control panel 42, one biopsy region from which a tissue sample will be removed.

When a desired biopsy region 54 has been selected, in step S9, the biopsy region position information calculator 94 calculates the three-dimensional position of the selected biopsy region 54, based on the position of the selected biopsy region 54 in the two radiographic images. The biopsy needle position information calculator 76 calculates the position of the tip end of the biopsy needle 52 before the biopsy needle 52 pierces the breast 22.

The traveled distance calculator 96 calculates the distance that the biopsy needle 52 moves with respect to the biopsy region 54, based on the three-dimensional position of the biopsy region 54, which has been calculated by the biopsy region position information calculator 94, the position of the tip end of the biopsy needle 52, which has been calculated by the biopsy needle position information calculator 76, the position of the opening 44, which has been detected by the opening detector 82, and the position of the compression plate 38, which has been calculated by the compression plate position information calculator 80.

In step S10, based on the calculated distance from the traveled distance calculator 96, the biopsy needle controller 74 moves the biopsy needle 52 in order to sample tissue from the biopsy region 54. The biopsy hand assembly 40 moves the first arm 48 and the second arm 50 in the X-Y plane, so as to position the biopsy needle 52 in a position confronting the biopsy region 54 (a position confronting the biopsy region 54 along directions indicated by the arrow Y). Then, in step S11, the biopsy hand assembly 40 moves the biopsy needle 52 in a direction indicated by the arrow Y, and inserts the biopsy needle 52 into the breast 22 through the opening 44 in the compression plate 38.

In step S12, when the sampler 56 of the biopsy needle 52 has reached a position near the biopsy region 54, the biopsy needle 52 starts to sample tissue from the biopsy region 54 under suction. Thereafter, in step S13, the biopsy needle controller 74 moves the biopsy needle 52 in an opposite direction, as indicated by the arrow Y, until the biopsy needle 52 is pulled out of the breast 22, whereupon the tissue sampling process is brought to an end.

With the mammographic apparatus 12 according to the present embodiment, as described above, the breast 22 of the examinee 20 is off-center in a direction along the chest wall 21 of the examinee 20 from a central position C of the image capturing base 36 near the chest wall 21. Then, the breast 22 is compressed and secured between the compression plate 38 and the image capturing base 36. The opening 44 defined in the compression plate 38 is positioned in confronting relation to the breast 22 having been off-center in the foregoing manner. In other words, while the central angle of the radiation source 26 and the central position C of the image capturing base 36 are aligned with the vertical axis 98, the breast 22 is displaced (off-center) from the vertical axis 98 along the chest wall 21 of the examinee 20, and the breast 22 is compressed and secured in position. The opening 44 also is displaced (off-center) so as to confront the breast 22, which has been displaced (off-center) from the vertical axis 98 along the chest wall 21.

Since the position of the examinee 20 with respect to the mammographic apparatus 12 also is off-center, when the radiation source housing unit 28 (the radiation source 26 and the collimator 30) is turned about the central position C from the central angle, the radiation source housing unit 28 is prevented from coming into contact with the examinee 20, who remains in a natural attitude in a sitting position. As a result, the examinee 20 can remain at a natural and comfortable attitude while the stereographic image capturing process is performed on the examinee 20, and while a tissue sample is removed from the biopsy region 54.

Since the examinable region of the biopsy region 54 is changed when the opening 44 is displaced (off-center) along the chest wall 21 of the examinee 20, the examinable region is virtually enlarged so as to increase the efficiency with which the biopsy region 54 can be examined. Furthermore, since the radiation detecting region (image capturing region) of the solid-state detector 34 changes when the breast 22 is displaced (off-center) along the chest wall 21 of the examinee 20, the radiation detecting region is virtually enlarged so as to increase the efficiency with which radiographic images can be captured using the FFDM mammographic apparatus 12.

As described above, inasmuch as the radiation source housing unit 28 is prevented from coming into contact with the examinee 20, who remains in a natural attitude in a sitting position while the radiation source housing unit 28 (the radiation source 26 and the collimator 30) is turned about the central position C from the central angle, the stereographic image capturing process can be performed reliably. Since the biopsy region position information calculator 94 calculates the three-dimensional position of the biopsy region 54 based on two radiographic images obtained by the stereographic image capturing process, the three-dimensional position of the biopsy region 54 can easily be calculated.

The radiation source housing unit 28 is turned to positions that are asymmetrical (unequal) with respect to right and the left sides of the examinee 20. Therefore, the radiation source housing unit 28 is more reliably prevented from coming into contact with the examinee 20 than if the radiation source housing unit 28 were turned to positions symmetrical with respect to right and left sides of the examinee, as in the related art. Accordingly, radiographic images of the examinee 20 can be captured, and a tissue sample can be removed from the examinee 20, without requiring the examinee 20 to assume an improper or uncomfortable attitude.

The traveled distance calculator 96 calculates the distance by which the biopsy needle 52 moves toward the three-dimensional position of the biopsy region 54, based on the position of the tip end of the biopsy needle 52, which has been calculated by the biopsy needle position information calculator 76, the three-dimensional position of the biopsy region 54, which has been calculated by the biopsy region position information calculator 94, the position of the opening 44, which has been detected by the opening detector 82, and the position of the compression plate 38, which has been calculated by the compression plate position information calculator 80. Based on the calculated distance that the biopsy needle 52 is intended to move, the biopsy hand assembly 40 and the biopsy needle controller 74 move the biopsy needle 52 to the biopsy region 54 in order to remove a tissue sample from the biopsy region 54. Consequently, a tissue sample can reliably and accurately be removed from the biopsy region 54.

Based on the position of the opening 44, which has been detected by the opening detector 82, and the position of the compression plate 38, which has been calculated by the compression plate position information calculator 80, the collimator 30 controls the irradiated field of the radiation 24, such that a portion of the breast 22 and the opening 44 will be included within the irradiated field. Accordingly, radiographic images of the breast 22 including the biopsy region 54 can be captured reliably.

In order to capture an ML view or an LM view, the breast 22 is compressed and secured between the image capturing base 36 and the compression plate 38, at a position off-center upwardly from the central position C. Further, the opening 44 is defined in the compression plate 38 so as to confront the off-center breast 22. Therefore, for capturing an ML view or an LM view, when the radiation source housing unit 28, the compression plate 38 and the image capturing base 36 are arranged in an array substantially horizontally along the directions indicated by the arrow Y, and the radiation source housing unit 28 is turned about the central position C from the central angle, the radiation source housing unit 28 is reliably prevented from coming into contact with the examinee 20. Consequently, the examinee 20 can assume a natural attitude during the process for capturing an ML view or an LM view.

Since the breast 22 is compressed and secured at a position off-center upwardly from the central position C, the examinee 20 can place her arms 102r, 102l above the image capturing base 36. Therefore, the examinee 20 can assume a comfortable attitude while the process for capturing an ML view or an LM view is performed on the examinee 20. Since the opening 44 is displaced in an upwardly off-center position, a tissue sample can reliably be removed from the biopsy region 54 of the breast 22, which has been off-center upwardly.

Characteristic functions of the present embodiment have been described above as being applied to a process for capturing an ML view or an LM view. However, the characteristic functions of the present embodiment also are applicable to a process of capturing a CC view or a process of capturing an MLO (MedioLateral Oblique) view, and can achieve the same advantages as those described above.

Figure 11A:
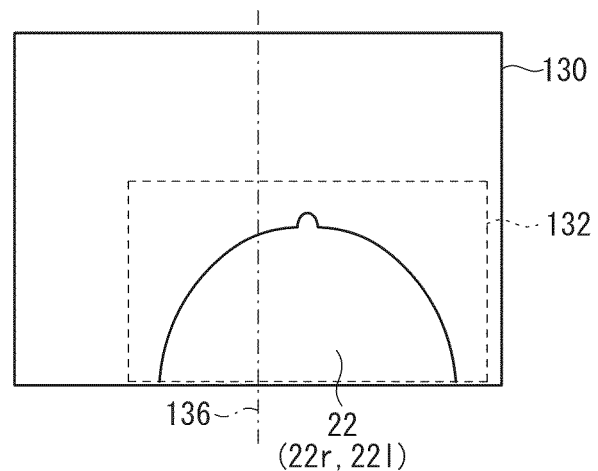
FIG. 11A is a view showing a corrected image.
Figure 11B:
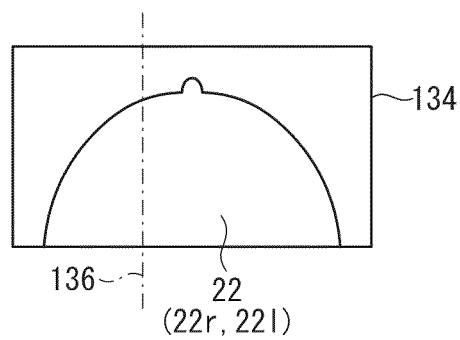
FIG. 11B is a view showing an image clipped from the corrected image shown in FIG. 11A.

The FFDM mammographic apparatus 12 includes a radiation detecting region, which is relatively large with respect to sizes of the compression plate 38 and the breast 22. As shown in FIG. 11A, when the breast 22, which is included in an image 130 output from the solid-state detector 34 to the detector controller 84, is small, a portion of the image 130 other than the breast 22 and the compression plate 38, i.e., a portion of the image 130 other than a to-be-clipped area 132 thereof, forms an unwanted area, which is not useful for enabling a doctor or radiological technician to select the biopsy region 54. In FIGS. 11A and 11B, the compression plate 38 has a central axis 136 along the swing shaft 16, and the vertical axis 98 (see FIGS. 4, 9A and 9B) extends perpendicularly to the central axis 136.

Figure 12:
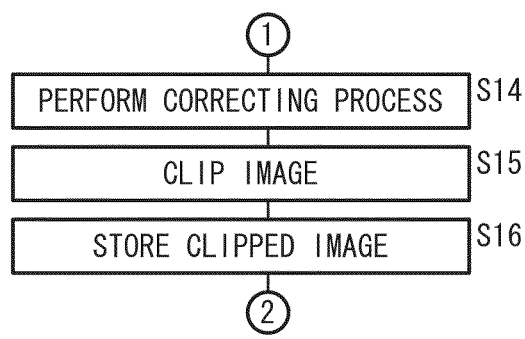
FIG. 12 is a flowchart of a process for generating the images shown in FIGS. 11A and 11B.

In step S14 shown in FIG. 12, which follows step S6 in FIG. 10, the detector controller 84 corrects a pixel area (unwanted area) of the image 130, other than the breast 22 and the compression plate 38. In step S15, the detector controller 84 designates a pixel area of the image 130, which includes the breast 22 as a to-be-clipped area 132, and clips the designated to-be-clipped area 132 from the image 130, thereby generating a new image 134. Thereafter, in step S16, the detector controller 84 stores the new image 134 in the image information storage unit 86. The CAD processor 88 then carries out the image processing process in step S7.

In step S15, the detector controller 84 (1) clips a to-be-clipped area 132 as a new image 134, having a pre-designated size depending on the type of compression plate 38. Alternatively, in step S15, the detector controller 84 (2) designates a to-be-clipped area 132 corresponding to the shape of the compression plate 38, and clips the designated to-be-clipped area 132 as a new image 134. Alternatively, in step S15, the detector controller 84 (3) aligns a to-be-clipped area 132 with the position of the compression plate 38, and clips the to-be-clipped area 132 as a new image 134.

As described above, the to-be-clipped area 132 is designated depending on the type, shape or position of the compression plate 38. The new image generated by clipping the designated to-be-clipped area 132 is stored in the image information storage unit 86. The new image 134 thus generated is free of an unwanted area, which a doctor or radiological technician does not need to take into account. As a result, the CAD processor 88 can clip only the relevant part of an image to be diagnosed by the doctor or radiological technician, i.e., a radiographic image including the biopsy region 54, within a short period of time. Since the detector controller 84 can process and correct the image 130, and thereafter clip the image 134 from the corrected image 130, the detector controller 84 can easily be instructed to perform the above clipping process, i.e., the process of designating the to-be-clipped area 132, and generate the image 134.

The mammographic apparatus 12 preferably has a plurality of compression plates 38, each having respective openings 44 defined at different positions thereon, wherein one of such compression plates 38 is used depending on the direction in which the breast 22 is to be imaged.

Because the compression plates 38 with openings 44 at different positions may be used selectively depending on various different image capturing methods including CC, ML, LM and MLO view capturing methods, the mammographic apparatus 12 can be used to image the breast 22, and also can remove a tissue sample from the breast 22 in any of desired directions.

The mammographic apparatus 12, which incorporates therein the biopsy apparatus 10 according to the present embodiment, has been described above. However, the present invention also may be applied to a mammographic apparatus, which is free of the biopsy hand assembly 40, the opening 44, the biopsy needle 52, the biopsy needle controller 74, the biopsy needle position information calculator 76, the opening detector 82, the biopsy region selector 92, and the traveled distance calculator 96. A mammographic apparatus that does not incorporate the biopsy apparatus 10 therein still has advantages that result from the other components, apart from those of the biopsy apparatus 10.

The mammographic apparatus 12 according to the present embodiment is not limited to the embodiment described above, but may be modified in various ways.

Modifications of the mammographic apparatus 12 according to the present embodiment, i.e., first through third modifications, will be described below with reference to FIGS. 13 through 18.

As shown in FIGS. 13 through 16, the first modification differs from the embodiment shown in FIGS. 1 through 12, in that the compression plate 38 comprises a frame 110, which extends in a substantially U-shaped form from the proximal end thereof that is held in interfitting engagement with the mount 58 (see FIG. 2), and a compression panel (plate-like member) 112 removably mounted on the frame 110.

The post 46 of the biopsy hand assembly 40 is mounted on the proximal end of the frame 110. The frame 110 has a groove 116 defined in inner side edges thereof and extending along the frame 110. The compression panel 112 is a substantially rectangular plate-like member, having an opening 44 defined therein near the chest wall 21 of the examinee 20, and an engaging key 114 disposed on three side edges of the compression panel 112, except for a side edge that faces the chest wall 21 of the examinee 20. The engaging key 114 is complementary in shape to the groove 116, and is removably engageable within the groove 116.

Figure 13:
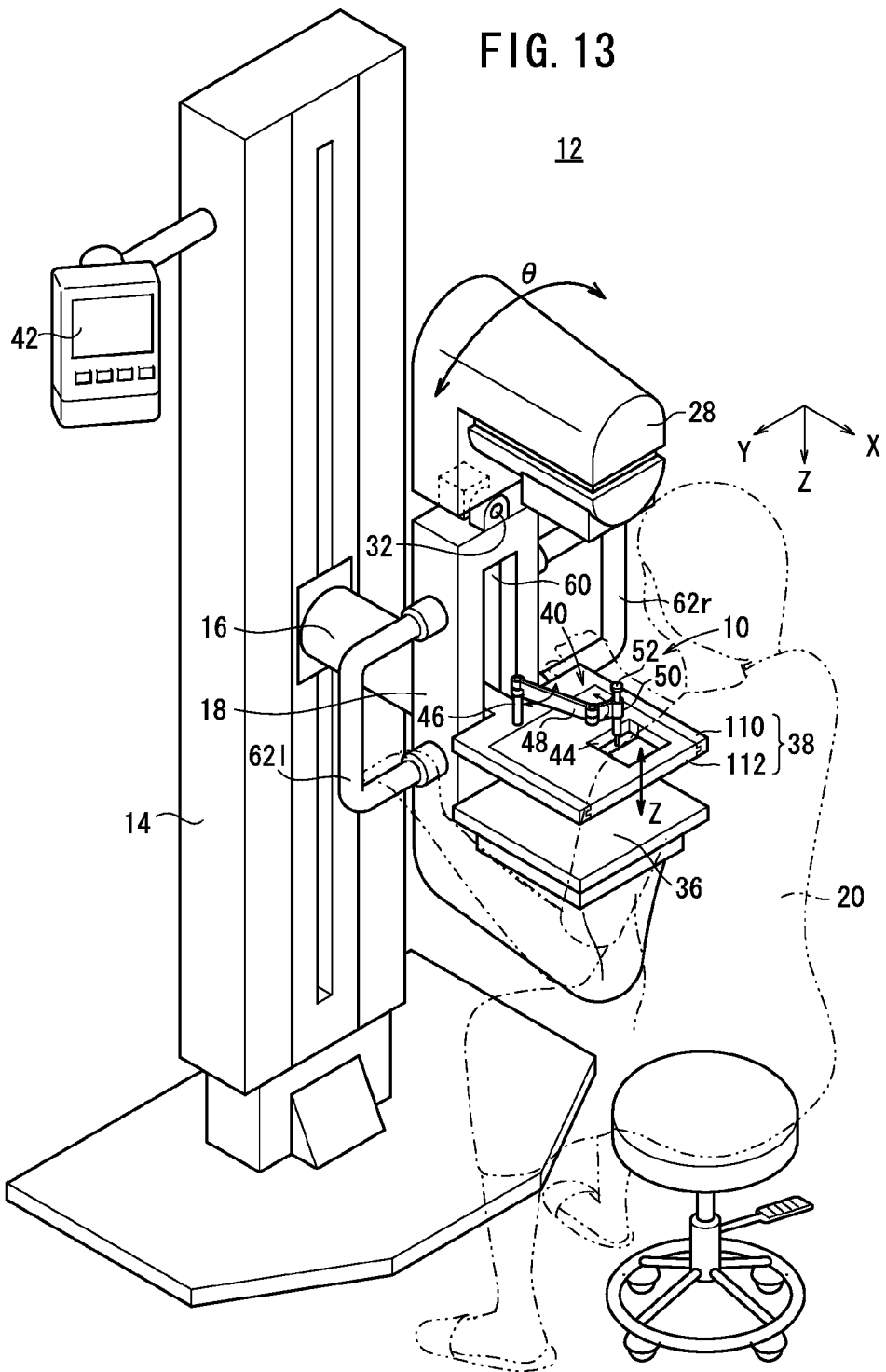
FIG. 13 is a perspective view of a first modification of the mammographic apparatus according to the present embodiment.
Figure 14:
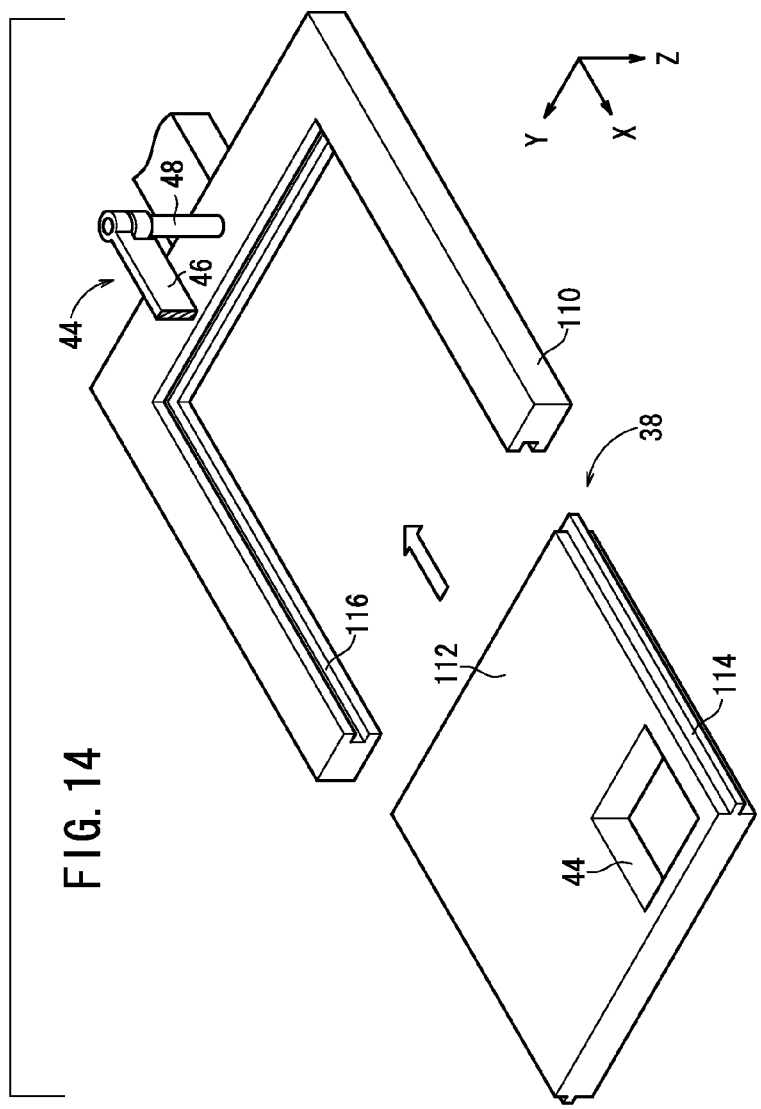
FIG. 14 is an enlarged perspective view of a compression plate shown in FIG. 13.
Figure 15:
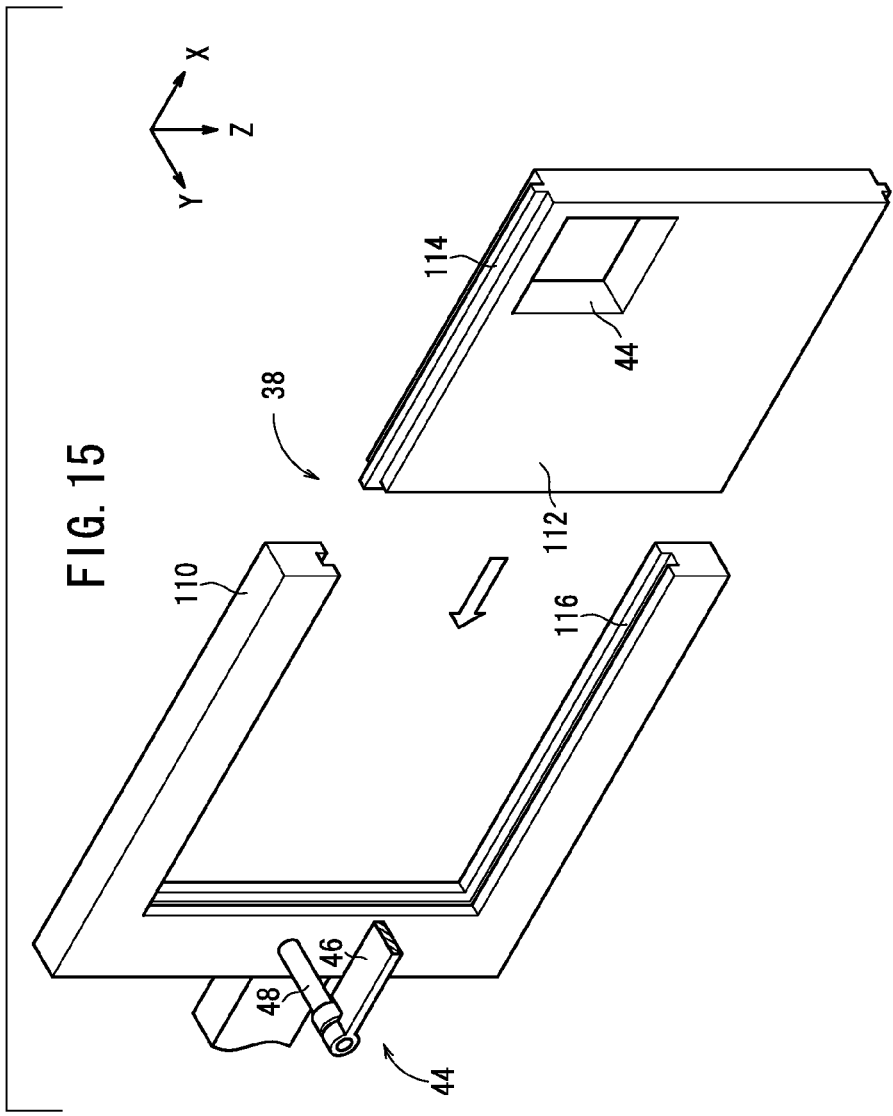
FIG. 15 is an enlarged perspective view of the compression plate shown in FIG. 13.
Figure 16:
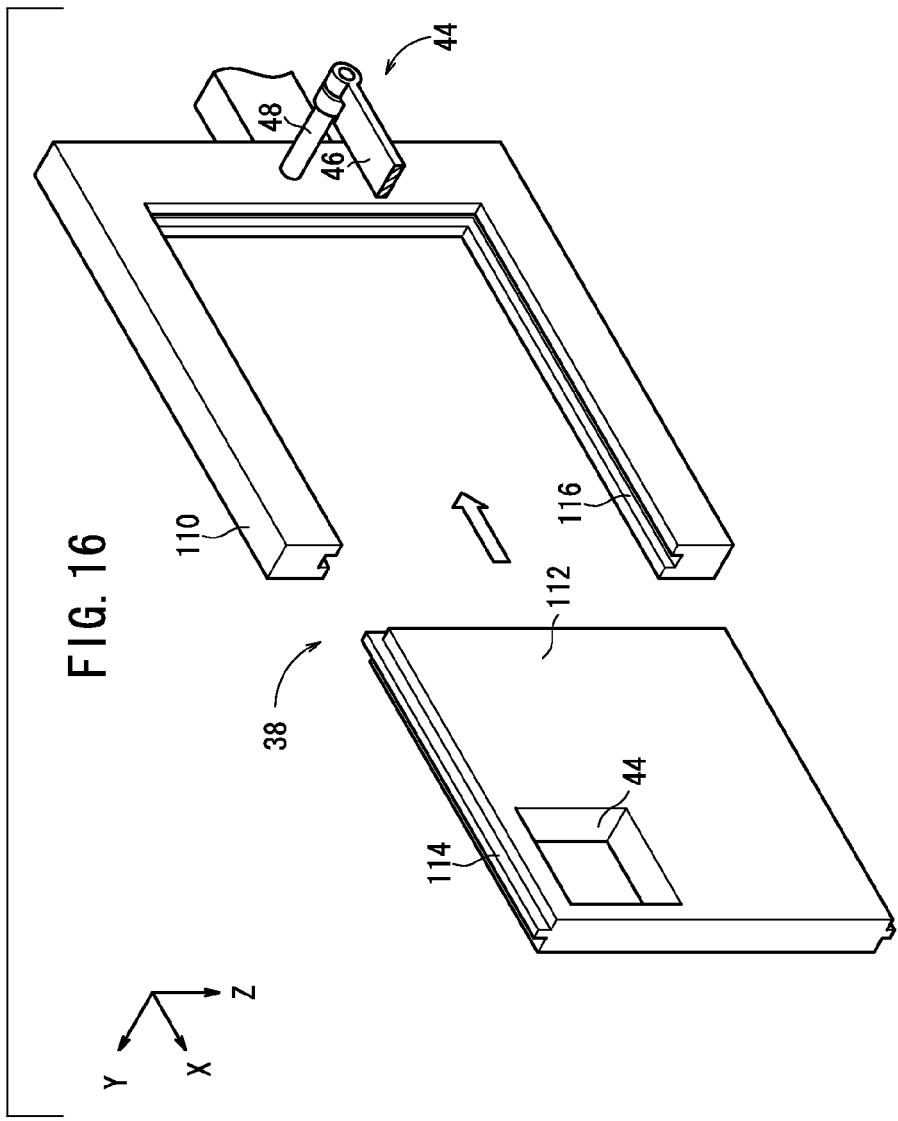
FIG. 16 is an enlarged perspective view of the compression plate shown in FIG. 13.

When the compression panel 112 is inserted from the position shown in FIGS. 14 through 16 into the frame 110 with the engaging key 114 engaging in the groove 116, the compression panel 112 and the frame 110 are combined with each other, as shown in FIG. 13. The breast 22 of the examinee can now be compressed and secured between the compression panel 112 and the image capturing base 36.

FIG. 14 shows the compression plate 38 oriented in a position for enabling capturing of a CC view. FIG. 15 shows the compression plate 38 oriented in a position for enabling capturing of an ML view. FIG. 16 shows the compression plate 38 oriented in a position for enabling capturing of an LM view.

According to the first embodiment, the compression panel 112, with the opening 44 defined therein, is mounted detachably on the frame 110. Therefore, the compression panel 112 can be inserted in a different orientation depending on the image capturing method used, whereby the number of compression plates 38 that the user has to provide is reduced.

More specifically, after an ML view capturing method is performed, the arm 18 is turned 180° about the swing shaft 16 in order to prepare the apparatus for an LM view capturing method. At this time, the opening 44, which was disposed on an upper position of the compression plate 38 in the ML view capturing method, now is positioned on a lower position of the compression plate 38. According to the first modification, the compression panel 112, with the opening 44 thereof in the lower position, is removed from the frame 110, turned upside down, and then inserted again into the frame 110, thereby placing the opening 44 in the upper position of the compression panel 112. Therefore, a doctor or radiological technician does not need to have two compression plates 38 with openings 44 in different positions, but rather, only one compression plate 38 may be used, as shown in FIGS. 14 through 16.

In order to carry out a CC view capturing method after an ML view capturing method, or to carry out an ML view capturing method or a CC view capturing method after an LM view capturing method, or to carry out a process of capturing an image of one of the breasts 22 in a CC view capturing method and thereafter capturing an image of the other breast 22 in a CC view capturing method, the compression panel 112 may be removed from the frame 110, turned upside down or inverted horizontally, and then be reinserted again into the frame 110.

According to the first modification, as described above, irrespective of whether an ML view capturing method, an LM view capturing method, or a CC view capturing method is carried out, there is no need to provide as many compression plates 38 as the image capturing methods. Rather, only one compression plate 38 is sufficient. Therefore, the mammographic apparatus 12 is relatively low in cost.

As shown in FIGS. 17A through 19C, the second modification differs from the embodiment shown in FIGS. 1 through 12 and the first modification shown in FIGS. 13 through 16, in that a dish (tissue holder) 120 for holding tissues 122 sampled by the biopsy needle 52 is disposed on an area of the compression plate 38, other than the opening 44 or the area of the compression plate 38 where the breast 22 is compressed and secured. Further, only the tissues 122 that are held in the dish 120 are irradiated with radiation 24.

Figure 17A:
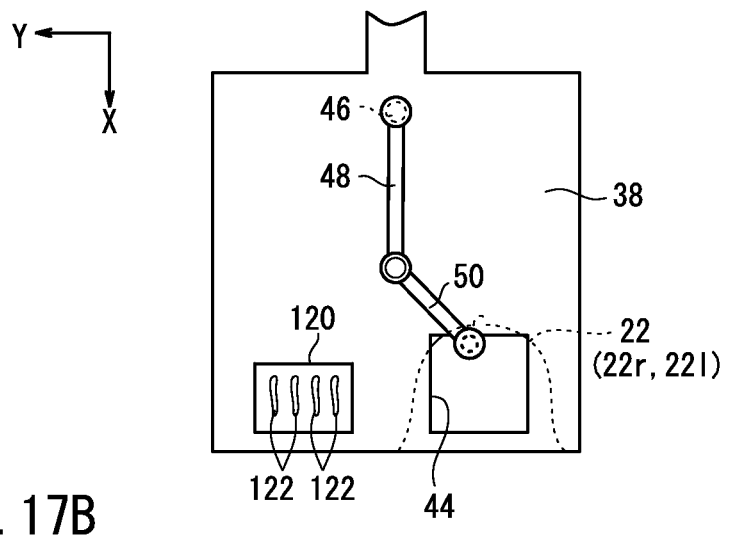
FIG. 17A is a partial plan view of a second modification of the mammographic apparatus according to the present embodiment.
Figure 17B:
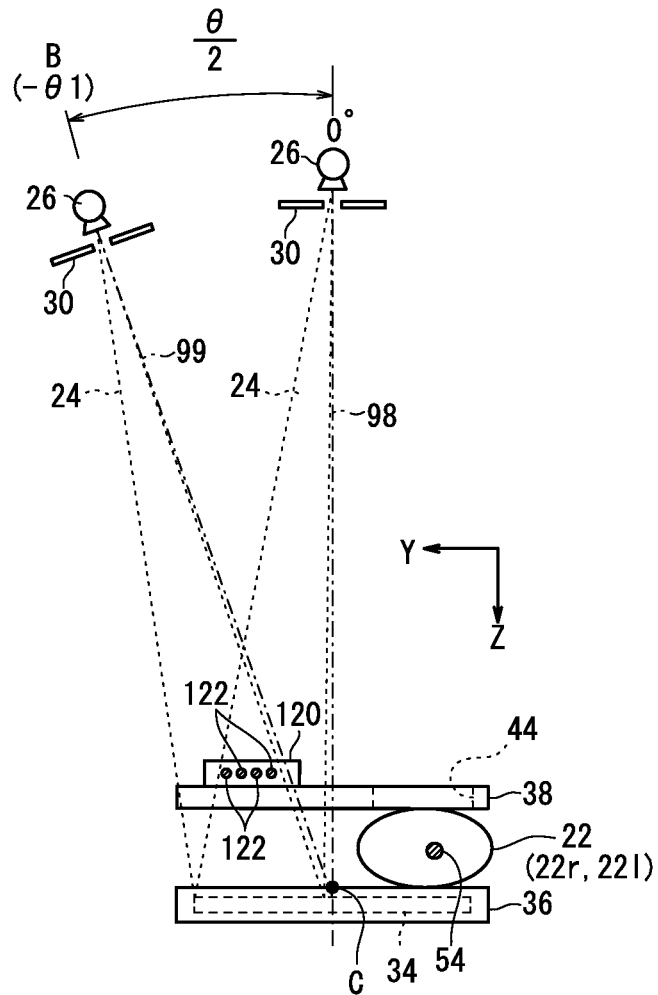
FIG. 17B is a schematic view illustrating a stereographic image capturing process carried out according to the second modification.

As shown in FIGS. 17A and 17B, after a stereographic image capturing process is carried out on the breast 22 in order to capture CC views, and after tissues 122 have been removed from the biopsy region 54 in the breast 22, the tissues 122 are placed in the dish 120, and the dish 120 is placed on the compression plate 38.

Figure 18:
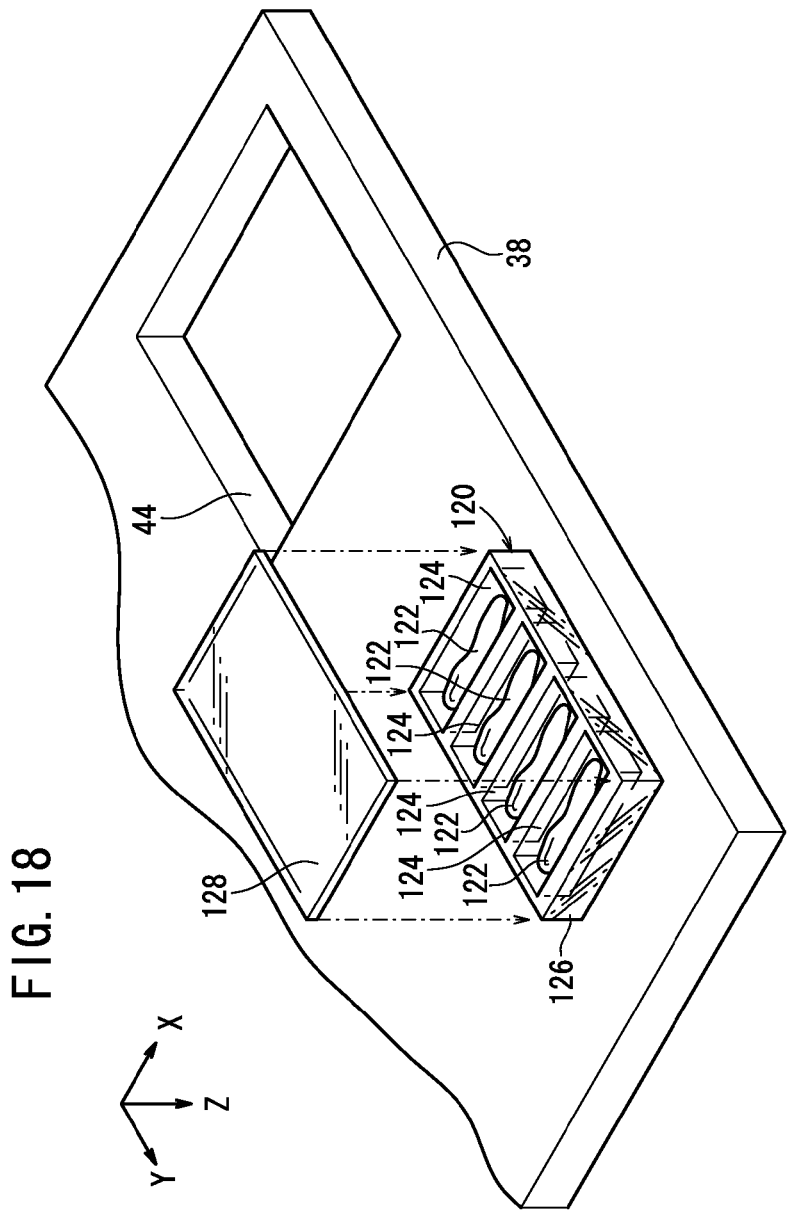
FIG. 18 is an enlarged fragmentary perspective view of a dish shown in FIGS. 17A and 17B.

As shown in FIG. 18, the dish 120 comprises a casing 126 having a plurality of holders 124 for holding respective tissues 122 therein, and a lid 128 that covers the upper end of the casing 126 for retaining the tissues 122 in the dish 120. The holders 124 are in the form of rectangular cavities defined in the casing 126, which are arrayed along the direction indicated by the arrow Y in FIG. 18.

According to the second modification, as shown in FIGS. 17A and 17B, a stereographic image capturing process is carried out only on tissues 122 that are held in the dish 120, and the tissues 122 are inspected to determine if such tissues 122 are desired tissues (calcified tissues) or not, based on two radiographic images obtained from the stereographic image capturing process.

More specifically, the mammographic apparatus 12 applies radiation 24 only to the tissues 122 that are held in the dish 120. At this time, in order to prevent the breast 22 from being irradiated with radiation 24, the radiation source 26 is disposed at the central angle and at the position B, while the collimator 30 controls the irradiation field of radiation 24 such that only the tissues 122 held in the dish 120 are included within the irradiation field.

Generally, tissues 122 sampled by the biopsy needle 52 are inspected by another (separate) inspection apparatus. According to the second modification, however, the dish 12 is placed in an area of the compression plate 38 other than the opening 44 thereof, whereby only the tissues 122 held in the dish 120 are irradiated with radiation 24. Radiation 24 that has passed through the tissues 122 is converted into radiographic images, and the tissues 122 are inspected to determine whether they are desired tissues or not based on the radiographic images.

Assuming that the tissues 122 are desired tissues, then the breast 22 can quickly be released from the compressed state between the compression plate 38 and the image capturing base 36. If the tissues 122 are not desired tissues, then tissues can immediately be sampled again from the breast 22. For economic reasons, some medical organizations (users) may find it difficult to provide another (separate) inspection apparatus. However, since the second modification does not require another inspection apparatus, but rather allows the mammographic apparatus 12 to inspect the sampled tissues 122, the second modification is highly cost-effective for such users.

Furthermore, since the collimator 30 controls the irradiation field of the radiation 24, such that only tissues 122 held in the dish 120 are included within the irradiation field, radiographic images can reliably be captured of tissues 122 that are held in the dish 120.

As has been described above, a plurality of tissues 122 are arrayed in the dish 120. However, in place thereof, a slide glass device (tissue holder) may be employed, which includes a glass cover placed over a tissue 122 to provide a prepared sample. The compression plate 38 including such a slide glass device offers the same advantages as those provided by the second modification.

Although the second modification has been described above with respect to a CC view capturing method, the second modification also may be applied to an ML view capturing method, an LM view capturing method, or an MLO view capturing method.

By way of example, certain structural details according to the second modification, which are applied to an ML view capturing method, will be described below with reference to FIGS. 19A through 19C.

Figure 19A:
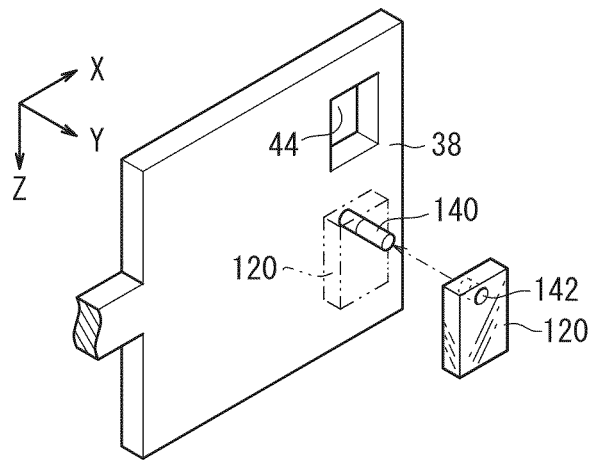
FIGS. 19A through 19C are perspective views showing the manner in which the second modification is applied to a stereographic image capturing process used for capturing an ML view.

As shown in FIG. 19A, a pin 140 that extends in the direction indicated by the arrow Y is mounted on an area of the compression plate 38 other than the opening 44 and the area thereof where the breast 22 is compressed and secured. The disk 120 has a hole 142 defined therein for enabling the pin 140 to be inserted therethrough. The disk 120 is disposed on the compression plate 38 in contact with the disk 120, and with the pin 140 extending through the hole 142. Therefore, the dish 120 is held on the compression plate 38 while the dish 120 hangs from the pin 140.

Figure 19B:
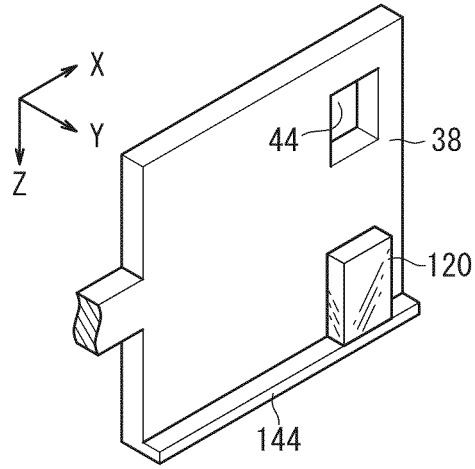

As shown in FIG. 19B, the compression plate 38 has a ledge 144 disposed along a side edge thereof (which is a lower side edge opposite to an upper side edge near the opening 44) in the direction indicated by the arrow Z, and projecting in a direction indicated by the arrow Y. The dish 120 is placed on the ledge 144 so as to lean against the compression plate 38.

Figure 19C:
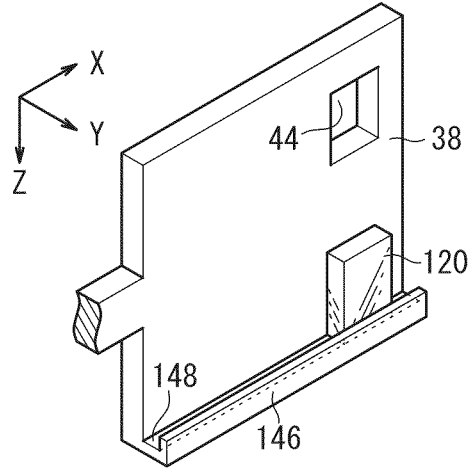

As shown in FIG. 19C, the compression plate 38 has a ledge 146 disposed along a side edge thereof in the direction indicated by the arrow Z, and projecting in the direction indicated by the arrow Y. The ledge 146 has a lip on a distal end thereof, which is bent upwardly. The ledge 146 and the compression plate 38 jointly define a groove 148 therebetween, which extends in the direction indicated by the arrow X. The dish 120 is inserted into the groove 148 so as to lean against the compression plate 38.

In either of the structures shown in FIGS. 19A through 19C, since the dish 120 is disposed within an area of the compression plate 38 other than the opening 44 and the area where the breast 22 is compressed and secured, a stereographic image capturing process can be carried out on tissues 122 held in the dish 120 in order to capture an ML view.

The second modification also may be applied to an LM view capturing method and an MLO view capturing method, by providing the compression plate 38 with the pin 140 and the ledges 144, 146, as shown in FIGS. 19A through 19C.

Figure 20:
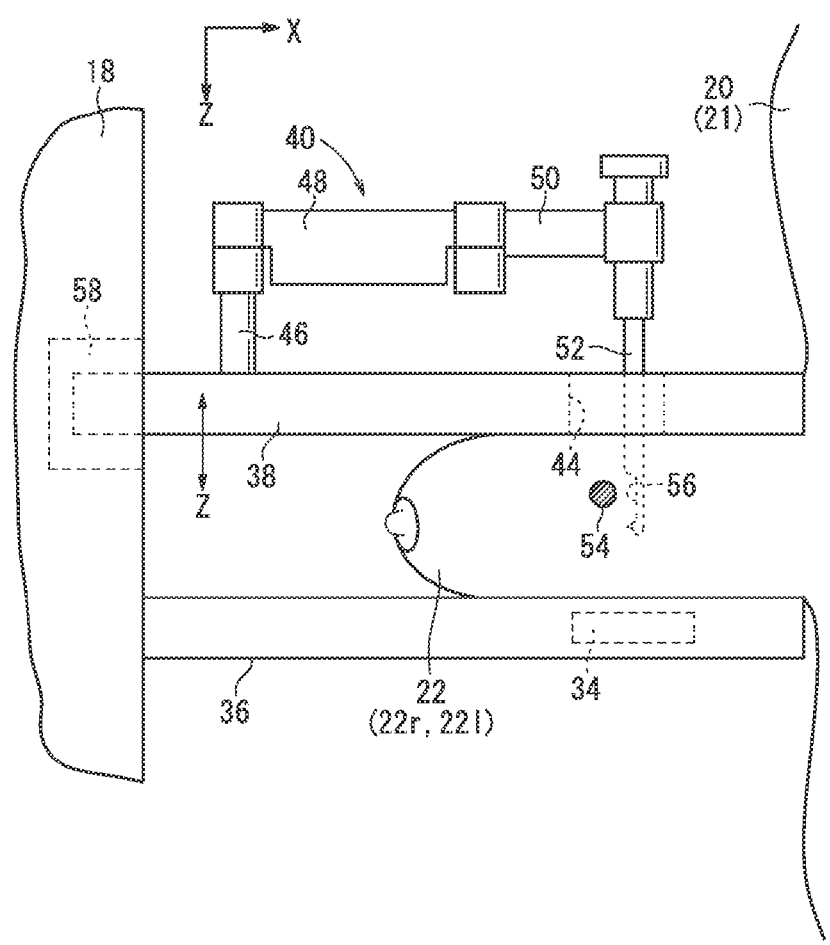
FIG. 20 is a fragmentary side elevational view of a third modification of the mammographic apparatus according to the present embodiment.

As shown in FIG. 20, the third modification differs from the embodiment shown in FIGS. 1 through 12, the first modification shown in FIGS. 13 through 16, and the second modification shown in FIGS. 17A through 19C, in that the third modification is applied to an SFDM mammographic apparatus 12, which incorporates a biopsy apparatus 10 therein.

In FIG. 20, the solid-state detector 34 has a relatively small radiation detecting region in conformity with the size of the opening 44. During a preparatory process for the stereographic image capturing process, the detector controller 84 (see FIG. 3) moves the solid-state detector 34 to a position (i.e., the position of the image capturing region, which depends on the irradiation field of the radiation 24) based on position information of the opening 44 as detected by the opening detector 82.

Therefore, the examinee 20 can assume a comfortable attitude, even when the affected region is imaged by an SFDM mammographic apparatus 12. Since the solid-state detector 34 is moved within the image capturing base 36 by the detector controller 84, it is possible for radiographic images of the breast 22 to be captured efficiently.

Although certain preferred embodiments of the present invention have been shown and described in detail, it should be understood that various changes and modifications may be made to the embodiments without departing from the scope of the invention as set forth in the appended claims.

What is claimed is:

1. A radiographic image capturing apparatus comprising:
    a radiation source adapted to apply radiation to an object to be examined of a subject;
    a radiation detector adapted to detect radiation that has passed through the object to be examined, and to convert the detected radiation into a radiographic image;
    an image capturing base housing the radiation detector therein; and
    a compression plate, which is displaceable toward the image capturing base, said compression plate adapted to compress and secure the object to be examined on the image capturing base, said compression plate having an opening defined therein so as to expose a portion of the object to be examined, the -opening being located offset from a center position of the compression plate in both a length direction and a width direction of the compression plate,
    wherein the compression plate and the image capturing base are adapted to secure the object to be examined therebetween at a position off-center from a central position of the image capturing base near the subject in a direction along the subject and off-center from a perpendicular axis of the image capturing base in a direction along the subject, the perpendicular axis passing through the central position,
    wherein the radiation source is adapted to be turned between a central angle and a predetermined angle that are asymmetrical with respect to the subject, the central angle being aligned with the perpendicular axis, the predetermined angle being spaced angularly about the central position from the central angle toward the object to be examined so as to confront the object to be examined, wherein the radiation source is configured to irradiate the object to be examined with the radiation from the central angle and the predetermined angle for capturing a stereographic image from the central angle and the predetermined angle, and
    wherein the radiation detector generates at least two radiographic images each corresponding to the central angle and the predetermined angle, and the radiographic image capturing apparatus further comprises a region-of-interest position information calculator adapted to calculate a three-dimensional position of a region of interest in the object to be examined based on the at least two radiographic images,
    said image capturing apparatus further comprising:
    an opening detector adapted to detect a position of the opening in the compression plate; and
    a radiation source energization control means for controlling an irradiation field based on the detected position of the compression plate opening, said irradiation field delimited by a collimator to delimit the irradiation field of the radiation such that at least the portion of the object to be examined and the opening are included within the irradiation field.

2. A radiographic image capturing apparatus according to claim 1, wherein the radiation source energization control means further controls the radiation source to irradiate the object to be examined with the radiation from the central angle and from the predetermined angle.

3. A radiographic image capturing apparatus according to claim 1, wherein:
    the image capturing base and the compression plate adapted to compress and secure a breast to be examined between the image capturing base and the compression plate, said compression plate being disposed above the capturing base and the compression plate is configured to move towards the image capturing base along the perpendicular axis.

4. A radiographic image capturing apparatus according to claim 1, wherein the compression plate opening is adapted to oppose a biopsy region of the object to be examined at the off-centered position,
    the radiographic image capturing apparatus further comprising a biopsy needle adapted to pass through the opening, adapted to pierce the biopsy region, and adapted to remove a tissue sample from the biopsy region, based on the at least two radiographic images.

5. A radiographic image capturing apparatus according to claim 4, further comprising a tissue holder for holding a portion of the tissue sample removed from the biopsy region by the biopsy needle,
    wherein the tissue holder is disposed in an area of the compression plate other than the opening,
    wherein the radiation source applies the radiation to the portion of the tissue sample that is held by the tissue holder, and
    wherein the radiation detector detects the radiation, which has passed through the portion of the tissue sample, and converts the detected radiation into a radiographic image.

* * * * *